(12) United States Patent
Bryan et al.

(10) Patent No.: US 8,962,038 B2
(45) Date of Patent: Feb. 24, 2015

(54) NITRITE FORMULATIONS AND THEIR USE AS NITRIC OXIDE PRODRUGS

(71) Applicants: Nathan S. Bryan, Houston, TX (US); Janet Zand, Austin, TX (US)

(72) Inventors: Nathan S. Bryan, Houston, TX (US); Janet Zand, Austin, TX (US)

(73) Assignees: Board of Regents, The University of Texas System, Austin, TX (US); Neogenis Labs, Inc., Austin, TX (US)

( * ) Notice: Subject to any disclaimer, the term of this patent is extended or adjusted under 35 U.S.C. 154(b) by 84 days.

(21) Appl. No.: 13/668,776

(22) Filed: Nov. 5, 2012

(65) Prior Publication Data

US 2013/0071494 A1  Mar. 21, 2013

Related U.S. Application Data

(63) Continuation of application No. 12/856,957, filed on Aug. 16, 2010, now Pat. No. 8,303,995, which is a continuation-in-part of application No. 12/484,364, filed on Jun. 15, 2009, now Pat. No. 8,298,589.

(60) Provisional application No. 61/061,251, filed on Jun. 13, 2008.

(51) Int. Cl.
| | |
|---|---|
| *A61K 31/195* | (2006.01) |
| *A61K 33/00* | (2006.01) |
| *A61K 36/00* | (2006.01) |
| *A61K 31/375* | (2006.01) |
| *A61K 45/06* | (2006.01) |

(52) U.S. Cl.
CPC ............ *A61K 33/00* (2013.01); *A61K 31/195* (2013.01); *A61K 31/375* (2013.01); *A61K 45/06* (2013.01); *A61K 36/00* (2013.01)
USPC ........................................... 424/718

(58) Field of Classification Search
None
See application file for complete search history.

(56) References Cited

U.S. PATENT DOCUMENTS

| | | | |
|---|---|---|---|
| 5,922,610 | A | 7/1999 | Alving et al. |
| 2001/0047035 | A1 | 11/2001 | Boykin |

FOREIGN PATENT DOCUMENTS

WO    WO-2010/141719 A2    12/2010

OTHER PUBLICATIONS

Prasad (Cardiovasc Drug Rev. 2006; 24(1):33-50).*
Alikulov et al., *Biol. Bull. Acad. Sci. USSR* 7(5):379-384 (Sep.-Oct. 1980) (abstract).
Becker et al., *Z. Kardiol.* 89(9):IX/88-IX/91 (2000).
Björne et al., *J. Clin. Invest.* 113(1):106-114 (Jan. 2004).
Bolli, *J. Mol. Cell Cardiol.* 33(11):1897-1918 (2001).
Brown et al., *Eur. J. Pharmacol.* 223(1):103-104 (1992).
Brown et al., *FEBS Letters* 356:295-298 (1994).
Bryan, *Free Radic. Biol. Med.* 41(5):691-701 (2006).
Bryan et al., *Nat. Chem. Biol.* 1(5):290-297 (Oct. 2005).
Bryan et al., *Proc. Natl. Acad. Sci. USA* 101(12):4308-4313 (Mar. 23, 2004).
Bryan et al., *Proc. Natl. Acad. Sci. USA* 104(48):19144-19149 (Nov. 27, 2007).

(Continued)

*Primary Examiner* — Ernest V Arnold
(74) *Attorney, Agent, or Firm* — Fulbright & Jaworski LLP

(57) ABSTRACT

Compositions comprising from about 40 weight parts to about 1000 weight parts of a botanical nitrate source; from about 20 weight parts to about 500 weight parts of a botanical source of nitrite reduction activity; and from about 4 weight parts to about 100 weight parts of a nitrite salt. Use of the composition in methods of reducing triglycerides or reducing C-reactive protein levels are also provided.

4 Claims, 8 Drawing Sheets

(56) References Cited

OTHER PUBLICATIONS

Castello et al., *Cell Metab.* 3(4):277-287 (Apr. 2006).
Chen et al., *J. Am. Med. Assoc.* 149(2):113-119 (May-Aug. 1952).
Cosby et al., *Nature Medicine* 9(12):1498-1505 (Dec. 2003).
Dejam et al., *Blood Cells Mol. Dis.* 32(3):423-429 (2004).
Dezfulian et al., *Cardiovascular Res.* 75(2):327-338 (2007).
Duncan et al., *Nat. Med.* 1(6):546-551 (Jun. 1995).
Duranski et al., *J. Clin. Invest.* 115(5):1232-1240 (May 2005).
Dykhuizen et al., *Antimicrob. Agents Chemother.* 40(6):1422-1425 (Jun. 1996).
Elrod et al., *Arterioscler. Thromb. Vasc. Biol.* 26(7):1517-1523 (2006).
Furchgott et al., *J. Pharcol. Exp. Ther.* 108(2):129-143 (1953).
Gladwin et al., *Nat. Chem. Biol.* 1(6):308-314 (Nov. 2005).
Goaz et al., *J. Dent. Res.* 40:355-365 (1961).
Grube et al., *The Biology of Nitric Oxide, Enzymology, Biochemistry, and Immunology*, S. Moncada, M. Feelisch, R. Busse and E.A. Higgs, London, Portland Press 4:201-204 (1994).
Hardwick et al., *Clin. Sci. (Lond.)* 100(4):395-400 (2001).
Hataishi et al., *Am. J. Physiol. Heart Circ. Physiol.* 291(1):H379-H384 (2006).
Herman et al., *Eur. Heart J.* 26(19):1945-1955 (2005).
Hunter et al., *Nat. Med.* 10(10):1122-1127 (Oct. 2004).
Ignarro, *J. Physiol. Pharmacol.* 53(4, Pt.1):503-514 (2002).
Ignarro et al., *Proc. Natl. Acad. Sci. USA* 84(24):9265-9269 (Dec. 1987).
Ishiwata et al., *J. Food Hyg. Soc. Jpn.* 16(2):89-92 (Apr. 1975).
Jones et al., *Am. J. Physiol. Heart Circ. Physiol.* 276(5, Pt. 2):H1567-H1573 (1999).
Jones et al., *Am. J. Physiol. Heart Circ. Physiol.* 286(1):H276-H282 (2004).
Kelm, *Biochim. Biophys. Acta* 1411:273-289 (1999).
Kelm et al., *The Biology of Nitric Oxide, Physiological and Clinical Aspects*, S. Moncada, M.A. Marletta, J.B. Hibbs, Jr. and E.A. Higgs, Eds., London, Portland Press 1:319-322 (1992).
Kelm et al., *Methods in Nitric Oxide Research*, M. Feelisch and J.S. Stamler, Eds., Chichester, John Wiley and Sons, pp. 47-58 (1996).
Kim-Shapiro et al., *Journal of Inorganic Biochemistry* 99:237-246 (2005).
Kleinbongard et al., *Free Radic. Biol. Med.* 40(2):295-302 (2006).
Kleinbongard et al., *Free Radic. Biol. Med.* 35(7):790-796 (2003).
Kozlov et al., *Shock* 15(5):366-371 (2001).
Kozlov et al., *FEBS Lett.* 454(1-2):127-130 (1999).
Lauer et al., *Proc. Natl. Acad. Sci. USA* 98(22):12814-12819 (Oct. 23, 2001).
Li et al., *J. Biol. Chem.* 279(17):16939-16946 (Apr. 23, 2004).
Li et al., *J. Biol. Chem.* 274(24):17325-17333 (Jun. 11, 1999).
Lundberg et al., *Arterioscler. Thromb. Vasc. Biol.* 25(5):915-922 (2005).
Ma et al., *Circ. Res.* 72(2):403-412 (1993).
McKnight et al., *Gut* 40(2):211-214 (1997).
Meah et al., *Food Addit. Contam.* 11(4):519-532 (1994).
Moncada et al., *Pharmacol. Rev.* 43(2):109-142 (1991).
Nohl et al., *Bioorg. Chem.* 29(1):1-13 (2001).
Nohl et al., *Acta Biochim. Pol.* 47(4):913-921 (2000).
Pabla et al., *Circ. Res.* 78(1):65-72 (1996).
Pique et al., *Eur. J. Pharmacol.* 174(2-3):293-296 (1989).
Pluta et al., *JAMA* 293(12):1477-1484 (Mar. 2005).
Reichert et al., *Am. J. Med. Sci.* 159:158-180 (1880).
Reutov et al., *Biochemistry (Mosc.)* 63(7):874-884 (1998).
Rhodes et al., *Biochem. Biophys. Res. Commun.* 209(2):590-596 (Apr. 17, 1995).
Sharp et al., *Am. J. Physiol. Heart Circ. Physiol.* 282(6):H2422-H2426 (2002).
Siegfried et al., *Am. J. Physiol.* 263(3, Pt. 2):H771-H777 (1992).
Spiegelhalder et al., *Food Cosmet. Toxicol.* 14:545-548 (1976).
Takehara et al., *Cell Struct. Funct.* 21(4):251-258 (1996).
Tannenbaum, *Science* 205(4413):1333-1335 (Sep. 28, 1979).
Tannenbaum et al., *J. Natl. Cancer Inst.* 53(1):79-84 (Jul. 1974).
Tischner et al., *FEBS Lett.* 576:151-155 (2004).
Tsuchiya et al., *Am. J. Physiol. Heart Circ. Physiol.* 288(5):H2163-H2170 (2005).
Vallance, *Gut* 40(2):288 (1997).
van Maanen et al., *Cancer Detect. Prev.* 20(6):590-596 (1996).
Walker et al., *Biochem. Soc. Trans.* 24(3):423S (1996).
Walters et al., *Biochim. Biophys. Acta* 143(2):310-318 (1967).
Webb et al., *Proc. Natl. Acad. Sci. USA* 101(37):13683-13688 (Sep. 14, 2004).
Yoshida et al., *Int. Arch. Occup. Environ. Health* 52:103-115 (1983).
Zweier et al., *Nat. Med.* 1(8):804-809 (Aug. 1995).
Bartsch et al., *Carcinogenesis* 5(11):1381-1393 (1984).
Bednar et al., *Plant Foods Hum. Nutr.* 45(1):71-80 (1994).
Benjamin et al., *Nature* 368(6471):502 (Apr. 7, 1994).
Boger et al., *Annu. Rev. Pharmacol. Toxicol.* 41:79-99 (2001).
Braunwald et al., *J. Clin. Invest.* 76(5):1713-1719 (Nov. 1985).
Bredt et al., *Proc. Natl. Acad. Sci. USA* 87(2):682-685 (Jan. 1990).
Comly, *JAMA* 129(2):112-116 (Sep. 8, 1945).
Craddock, *Nature* 306:638 (Dec. 15, 1983).
Donahoe, *Pediatrics* 3:308-311 (1949).
Druckrey et al., *Naturwissenschaften* 49:498-499 (1962).
Ender et al., *Naturwissenschaften* 51:637-638 (1964).
Esper et al., *Cardiovasc. Diabetol.* 5:4 (Feb. 23, 2006).
Feelisch et al., *J. Biol. Chem.* 283(49):33927-33934 (Dec. 5, 2008).
Gold et al., *Biochem. Biophys. Res. Commun.* 164(2):714-721 (Oct. 31, 1989).
Green et al., *Proc. Natl. Acad. Sci. USA* 78(12):7764-7768 (Dec. 1981).
Hogg, *Free Radic. Biol. Med.* 28(10):1478-1486 (2000).
Hord et al., *Am. J. Clin. Nutr.* 90(1):1-10 (2009).
Jansson et al., *Nat. Chem. Biol.* 4(7):411-417 (Jul. 2008).
Kross et al., *Am. J. Public Health* 83(2):270-272 (Feb. 1993).
Lecks, *Am. J. Dis. Child.* 79:117-123 (1950).
Liu et al., *Methods Enzymol.* 268:311-324 (1996).
Lundberg et al., *Free Radic. Biol. Med.* 37(3):395-400 (2004).
Lundberg et al., *Nat. Rev. Microbiol.* 2(7):593-602 (Jul. 2004).
Lundberg et al., *Gut* 35(11):1543-1546 (1994).
Magee et al., *Br. J. Cancer* 10(1):114-122 (1956).
McCord et al., *Adv. Myocardiol.* 5:183-189 (1985).
Moncada et al., *N. Engl. J. Med.* 329(27):2002-2012 (Dec. 30, 1993).
Myerburg, *J. Cardiovasc. Electrophysiol.* 12(3):369-381 (Mar. 2001).
Nayler, *Am. J. Pathol.* 102(2):262-270 (Feb. 1981).
Sander et al., *Arzneimittel-Forsch.* 19:1091-1093 (Jul. 1969).
Schulman et al., *JAMA* 295(1):58-64 (2006).
Sobko et al., *Am. J. Physiol. Gastrointest. Liver Physiol.* 287(5):G993-G997 (Nov. 2004).
Tang et al., *Free Radic. Biol. Med.* 47(6):835-840 (2009).
Tannenbaum et al., *Science* 200:1487-1489 (Jun. 30, 1978).
Walker, *Biochem. Soc. Trans.* 24(3):780-785 (Aug. 1996).
Ward et al., *Environ. Health Perspect.* 113(11):1607-1614 (Nov. 2005).
Weller et al., *J. Invest. Dermatol.* 107(3):327-331 (1996).
Wennmalm et al., *Cir. Res.* 73(6):1121-1127 (Dec. 1993).
Widlansky et al., *J. Am. Coll. Cardiol.* 42(7):1149-1160 (2003).
Windmueller et al., *Am. J. Physiol.* 241(6):E473-E480 (1981).

\* cited by examiner

A

B

C

D

US 8,962,038 B2

NITRITE FORMULATIONS AND THEIR USE AS NITRIC OXIDE PRODRUGS

RELATED APPLICATIONS

This application is a continuation of U.S. patent application Ser. No. 12/856,957, filed on Aug. 16, 2010, which was a continuation-in-part of U.S. patent application Ser. No. 12/484,364, filed on Jun. 15, 2009, which claims priority to U.S. Provisional Patent Application Ser. No. 61/061,251, filed on Jun. 13, 2008, all of which applications are incorporated herein by reference in their entirety.

BACKGROUND OF THE INVENTION

Field of the Invention

The present invention relates generally to the field of cardiovascular health and performance. More particularly, several embodiments of the invention relate to nitrite formulations and their use as nitric oxide prodrugs.

SUMMARY OF THE INVENTION

In one embodiment, the present invention is directed to a composition, comprising from about 40 weight parts to about 1000 weight parts of a botanical nitrate source; from about 20 weight parts to about 500 weight parts of a botanical source of nitrite reduction activity; and from about 4 weight parts to about 100 weight parts of a nitrite salt In one embodiment, the present invention is directed to a method of reducing a patient's triglyceride level, comprising administering to the patient a composition in a form of a lozenge dissolvable in the mouth, the composition comprising from about 40 weight parts to about 1000 weight parts of a botanical nitrate source; from about 20 weight parts to about 500 weight parts of a botanical source of nitrite reduction activity; from about 20 weight parts to about 500 weight parts L-citrulline; and from about 4 weight parts to about 100 weight parts of a nitrite salt.

In one embodiment, the present invention is directed to a method of reducing a patient's C-reactive protein level, comprising administering to the patient a composition in a form of a lozenge dissolvable in the mouth, the composition comprising from about 40 weight parts to about 1000 weight parts of a botanical nitrate source; from about 20 weight parts to about 500 weight parts of a botanical source of nitrite reduction activity; from about 20 weight parts to about 500 weight parts L-citrulline; and from about 4 weight parts to about 100 weight parts of a nitrite salt.

BRIEF DESCRIPTION OF THE DRAWINGS

The following drawings form part of the present specification and are included to further demonstrate certain aspects of the present invention according to several embodiments disclosed herein. The invention according to several embodiments disclosed herein may be better understood by reference to one or more of these figures in combination with the detailed description of specific embodiments presented herein.

DESCRIPTION OF ILLUSTRATIVE EMBODIMENTS

Significance

Figure 1:
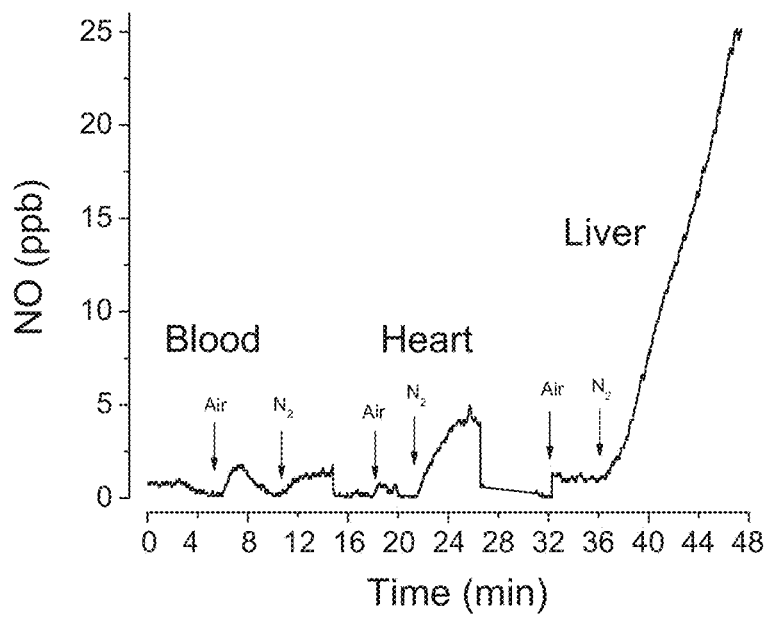
FIG. 1. (top) Original tracing from blood and tissue aerobic and anaerobic nitrite reduction to NO. (bottom) Quantification of NO generation from nitrite under aerobic and anaerobic conditions in blood and tissues after the addition of 200 µM nitrite. Data represent n=3-4 for each tissue and NO quantified over 4 minutes. Inset: Compartment-specific fold increase from aerobic to anaerobic NO formation from nitrite.
Figure 1:
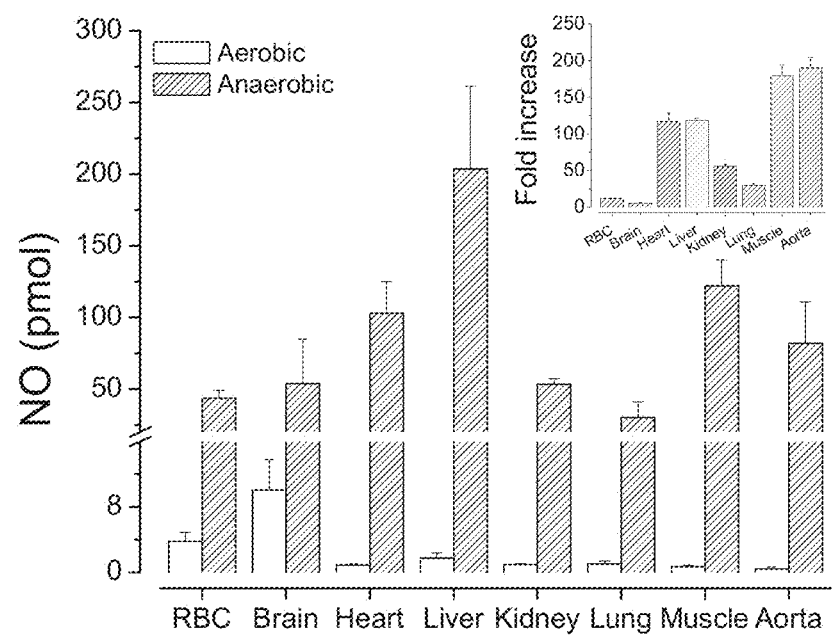

All life requires nitrogen-compounds. Nitrite ($NO_2$—) is such a compound that is naturally occurring in nature and biology. Over the years, the pharmacological stance on nitrite has undergone a surprising metamorphosis, from a vilified substance that generates carcinogenic nitrosamines in the stomach, to a life-saving drug that liberates a protective agent (NO) during hypoxic events. Nitrite has been investigated as a vasodilator in mammals for over 125 years and is a known by-product of organic nitrate metabolism. There has been a recent re-discovery of some of the vasodilator actions of nitrite in physiology along with novel discoveries which may render nitrite a fundamental molecule in biology. Nitrite is emerging as an endogenous signaling molecule and regulator of gene expression that can not only serve as a diagnostic marker but also as potential therapy of cardiovascular disease. Up until recently nitrite was thought to be an inert oxidative breakdown product of endogenous nitric oxide synthesis.

Certain embodiments of the present invention disclosed herein provide a formulation and a process to enhance and extend the therapeutic half-life of nitrite and therefore increase nitric oxide (NO) bioavailability. Thus, several embodiments provide the basis for new preventive or therapeutic strategies in diseases associated with NO insufficiency and new guidelines for optimal health as well as extend the therapeutic window in which one may intervene during a heart attack. Extension of nitrite half-life is desirable in the design of cardioprotective therapeutics or preventative medicines. As such, several embodiments prevent the onset or progression of cardiovascular or heart disease and protect from myocardial infarction thru nitrite/nitrate supplementation. Furthermore, certain embodiments provide an extended half-life of nitrite, out to 1 hour, which is the "golden hour" in terms of recovery from heart attack and stroke. The possibility of modulating an endogenous signaling pathway (NO) known to be involved in many physiological and pathophysiological events through a molecule found in certain foods is revolutionary and intriguing.

Nitrite, NO and Cardiovascular Disease

Ischemic heart disease, including myocardial infarction, remains the leading cause of morbidity and mortality in all industrialized nations (Myerburg, R. J. (2001). "Sudden cardiac death: exploring the limits of our knowledge." *J Cardiovasc Electrophysiol* 12(3): 369-81). There are two distinct components of damage to the heart in patients who experience acute myocardial infarction: ischemic injury and reperfusion injury. The myocardium is able to tolerate brief periods of ischemia (an absolute or relative shortage of the blood supply to an organ) as activation of inherent, adaptive mechanisms can preserve energy levels and prevent injury. These include switching metabolism to anaerobic glycolysis and fatty acid utilization, increasing glucose uptake, and decreasing contractility. If ischemia persists however, the myocardium will develop a severe adenosine tri-phosphate (ATP) deficit, resulting in irreversible injury and culminating in cell death. Although reperfusion of ischemic tissues provides oxygen and metabolic substrates necessary for the recovery and survival of reversibly injured cells, reperfusion itself paradoxically results in the acceleration of cellular necrosis (Braunwald, E. and R. A. Kloner (1985). "Myocardial reperfusion: a double-edged sword?" *J Clin Invest* 76(5): 1713-9). Reperfusion is characterized by the formation of oxygen radicals upon reintroduction of molecular oxygen to ischemic tissues, resulting in widespread lipid and protein oxidative modifications, mitochondrial injury, as well as tissue apoptosis and necrosis (Nayler, W. G. (1981). "The role of calcium in the ischemic myocardium." *Am J Pathol* 102(2): 262-70; McCord, J. M., R. S. Roy, et al. (1985). "Free radicals and myocardial ischemia. The role of xanthine oxidase." *Adv Myocardiol* 5: 183-9).

The loss of nitric oxide (NO) generation as a result of a dysfunctional vascular endothelium is a very likely cause of heart disease (Esper, R. J., R. A. Nordaby, et al. (2006). "Endothelial dysfunction: a comprehensive appraisal." *Cardiovasc Diabetol* 5: 4). Continuous generation of NO is essential for the integrity of the cardiovascular system and a decreased production and/or bioavailability of NO is central to the development of cardiovascular disorders (Ignarro, L. J. (2002). "Nitric oxide as a unique signaling molecule in the vascular system: a historical overview." *J Physiol Pharmacol* 53(4 Pt 1): 503-14; Herman, A. G. and S. Moncada (2005). "Therapeutic potential of nitric oxide donors in the prevention and treatment of atherosclerosis." *Eur Heart J* 26(19): 1945-55). NO is a highly reactive and diffusible gas formed by three NO synthase (NOS) isoforms: neuronal NOS (nNOS), endothelial NOS (eNOS), and inducible NOS (iNOS). NO has been extensively studied in the setting of ischemia-reperfusion (ischemia/reperfusion) injury. Previous studies clearly demonstrate that the deficiency of eNOS exacerbates myocardial ischemia/reperfusion injury (Jones, S. P., W. G. Girod, et al. (1999). "Myocardial ischemia-reperfusion injury is exacerbated in absence of endothelial cell nitric oxide synthase." *Am J Physiol* 276(5 Pt 2): H1567-73; Sharp, B. R., S. P. Jones, et al. (2002). "Differential response to myocardial reperfusion injury in eNOS-deficient mice." *Am J Physiol Heart Circ Physiol* 282(6): H2422-6), whereas the overexpression of eNOS (Jones, S. P., J. J. Greer, et al. (2004). "Endothelial nitric oxide synthase overexpression attenuates myocardial reperfusion injury." *Am J Physiol Heart Circ Physiol* 286(1): H276-82; Elrod, J. W., J. J. Greer, et al. (2006). "Cardiomyocyte-specific overexpression of NO synthase-3 protects against myocardial ischemia-reperfusion injury." *Arterioscler Thromb Vasc Biol* 26(7): 1517-23), NO donor (Siegfried, M. R., C. Carey, et al. (1992). "Beneficial effects of SPM-5185, a cysteine-containing NO donor in myocardial ischemia-reperfusion." *Am J Physiol* 263(3 Pt 2): H771-7; Pabla, R., A. J. Buda, et al. (1996). "Nitric oxide attenuates neutrophil-mediated myocardial contractile dysfunction after ischemia and reperfusion." *Circ Res* 78(1): 65-72) or inhaled NO gas (Hataishi, R., A. C. Rodrigues, et al. (2006). "Inhaled nitric oxide decreases infarction size and improves left ventricular function in a murine model of myocardial ischemia-reperfusion injury." *Am J Physiol Heart Circ Physiol* 291(1): H379-84) therapy significantly protect the myocardium (Bolli, R. (2001). "Cardioprotective function of inducible nitric oxide synthase and role of nitric oxide in myocardial ischemia and preconditioning: an overview of a decade of research." *J Mol Cell Cardiol* 33(11): 1897-918). NO possesses a number of physiological properties that makes it a potent cardioprotective-signaling molecule. These include vasodilation and the inhibition of oxidative stress, platelet aggregation, leukocyte chemotaxis and apoptosis (Ignarro, L. J., G. M. Buga, et al. (1987). "Endothelium-derived relaxing factor produced and released from artery and vein is nitric oxide." *Proc Natl Acad Sci USA* 84(24): 9265-9; X. L., A. S. Weyrich, et al. (1993). "Diminished basal nitric oxide release after myocardial ischemia and reperfusion promotes neutrophil adherence to coronary endothelium." *Circ Res* 72(2): 403-12; Li, J., C. A. Bombeck, et al. (1999). "Nitric oxide suppresses apoptosis via interrupting caspase activation and mitochondrial dysfunction in cultured hepatocytes." *J Biol Chem* 274(24): 17325-33). NO synthesis is influenced by various cofactors such as tetrahydrobiopterin, flavin mononucleotide and flavin adenine dinucleotide, the presence of reduced thiols, the endogenous NOS inhibitor asymmetric dimethylarginine (ADMA) and substrate and oxygen availability. Without an adequate delivery of substrate and co-factors (conditions that exist during ischemia), NOS no longer produces NO but instead transfers the free electrons to oxygen and thus produces free oxygen radicals (Becker, B. F., C. Kupatt, et al. (2000). "Reactive oxygen species and nitric oxide in myocardial ischemia and reperfusion." *Z Kardiol* 89 Suppl 9: 1X/88-91, hereby incorporated by reference herein). Thus, there is a need for additional NO production in ischemic tissues that may limit ischemia/reperfusion injury.

Nitrite is an oxidative breakdown product of NO that has been shown to serve as an acute marker of NO flux/formation (Kleinbongard, P., A. Dejam, et al. (2003). "Plasma nitrite reflects constitutive nitric oxide synthase activity in mammals." *Free Radic Biol Med* 35(7): 790-6). Nitrite has recently moved to the forefront of NO biology (Gladwin, M. T., A. N. Schechter, et al. (2005). "The emerging biology of the nitrite anion." *Nat Chem Biol* 1(6): 308-14), as it represents a major storage form of NO in blood and tissues (Bryan, N. S. (2006). "Nitrite in nitric oxide biology: cause or consequence? A systems-based review." *Free Radic Biol Med* 41(5): 691-701, hereby incorporated by reference herein). In addition to the oxidation of NO, nitrite is also derived from reduction of salivary nitrate by commensal bacteria in the mouth and gastrointestinal tract (Tannenbaum, S. R., A. J. Sinskey, et al. (1974). "Nitrite in human saliva. Its possible relationship to nitrosamine formation." *J Natl Cancer Inst* 53: 79-84; van Maanen, J. M., A. A. van Geel, et al. (1996). "Modulation of nitrate-nitrite conversion in the oral cavity." *Cancer Detect Prev* 20(6): 590-6) as well as from dietary sources such as meat, vegetables and drinking water. Much of the recent focus on nitrite physiology is due to its ability to be reduced to NO during ischemic or hypoxic events (Zweier, J. L., P. Wang, et al. (1995). "Enzyme-independent formation of nitric oxide in biological tissues." *Nat Med* 1(8): 804-9; Bryan, N. S., T. Rassaf, et al. (2004). "Cellular Targets and Mechanisms of Nitros(yl)ation: An Insight into Their Nature and Kinetics in vivo." *Proc. Natl. Acad Sci. USA* 101(12): 4308-4313, hereby incorporated by reference herein; Lundberg, J. O. and E. Weitzberg (2005). "NO generation from nitrite and its role in vascular control." *Arterioscler Thromb Vasc Biol* 25(5): 915-22; Bryan 2006). Nitrite reductase activity in mammalian tissues has been linked to the mitochondrial electron transport system (Walters, C. L., R. J. Casselden, et al. (1967). "Nitrite metabolism by skeletal muscle mitochondria in relation to haem pigments." *Biochim Biophys Acta* 143(2): 310-8; Reutov, V. P. and E. G. Sorokina (1998). "NO-synthase and nitrite-reductase components of nitric oxide cycle." *Biochemistry (Mosc)* 63(7): 874-84; Kozlov, A. V., K. Staniek, et al. (1999). "Nitrite reductase activity is a novel function of mammalian mitochondria." *FEBS Lett* 454(1-2): 127-30), protonation (Zweier, Wang et al. 1995), deoxyhemoglobin (Cosby, K., K. S. Partovi, et al. (2003). "Nitrite reduction to nitric oxide by deoxyhemoglobin vasodilates the human circulation." *Nature Medicine* 9: 1498-1505, hereby incorporated by reference herein), and xanthine oxidase (Alikulov, Z. A., P. L'Vov N, et al. (1980). "[Nitrate and nitrite reductase activity of milk xanthine oxidase]." *Biokhimiia* 45(9): 1714-8; Li, H., A. Samouilov, et al. (2004). "Characterization of the effects of oxygen on xanthine oxidase-mediated nitric oxide formation." *J Biol Chem* 279(17): 16939-46; Webb, A., R. Bond, et al. (2004). "Reduction of nitrite to nitric oxide during ischemia protects against myocardial ischemia-reperfusion damage." *Proc Natl Acad Sci U S A* 101(37): 13683-8). Nitrite can also transiently form nitrosothiols (RSNOs) under both normoxic and hypoxic conditions (Bryan, Rassaf et al. 2004) and a recent study by Bryan et al demonstrates that steady state concentrations of tissue nitrite and nitroso are affected by changes in dietary NOx (nitrite and nitrate) intake (Bryan, N. S., B. O. Fernandez, et al. (2005). "Nitrite is a signaling molecule and regulator of gene expression in mammalian tissues." *Nat Chem Biol* 1(5): 290-7, hereby incorporated by reference herein). Previous studies have shown that nitrite therapy prior to reperfusion protects against hepatic and myocardial ischemia/reperfusion injury (Webb, Bond et al. 2004; Duranski, M. R., J. J. Greer, et al. (2005). "Cytoprotective effects of nitrite during in vivo ischemia-reperfusion of the heart and liver." *J Clin Invest* 115(5): 1232-1240). Additionally, experiments in primates revealed a beneficial effect of long-term application of nitrite on cerebral vasospasm (Pluta, R. M., A. Dejam, et al. (2005). "Nitrite infusions to prevent delayed cerebral vasospasm in a primate model of subarachnoid hemorrhage." *Jama* 293(12): 1477-84). Oral nitrite has also been shown to reverse L-NAME induced hypertension and serve as an alternate source of NO in vivo (Tsuchiya, K., Y. Kanematsu, et al. (2005). "Nitrite is an alternative source of NO in vivo." *Am J Physiol Heart Circ Physiol* 288(5): H2163-70).

A reduced NO availability is a hallmark of a number of cardiovascular disorders. Hyperlipidemia, arterial hypertension, diabetes, smoking and aging are major risk factors for the manifestation of cardiovascular events (Widlansky, M. E., N. Gokce, et al. (2003). "The clinical implications of endothelial dysfunction." *J. Am Coll Cardiol* 42: 1149-1160). Plasma nitrite reflects acute changes in endothelial NOS activity in various mammals (Kleinbongard, Dejam et al. 2003) and thus may provide an accurate measurement of patients at risk for cardiovascular events. A recent report by Kleinbongard et al. (Kleinbongard, P., A. Dejam, et al. (2006). "Plasma nitrite concentrations reflect the degree of endothelial dysfunction in humans." *Free Radic Biol Med* 40(2): 295-302), demonstrated that plasma nitrite levels progressively decrease with increasing cardiovascular risk load. Risk factors considered include age, hypertension, smoking, and hypercholesterolemia. Since nitrite acts as a protective molecule during ischemic events these data raise the intriguing possibility that the underlying problem with these patients is their diminished nitrite bioavailability. Since a substantial portion of steady state nitrite concentrations in blood and tissue are derived from dietary sources (Bryan, Fernandez et al. 2005), modulation of nitrite and/or nitrate intake may provide a first line of defense for ischemic heart disease.

Therefore, several embodiments increase nitrite availability through diet or supplementation and provide an alternate route to increased NO availability as well as conferring protection from ischemia/reperfusion injury or other adverse cardiovascular event (e.g., heart attack, stroke, etc.). Since the half life of nitrite is on the order of seconds, it can only be used acutely and repeatedly for any therapeutic benefit. Dietary nitrite and nitrate supplementation for 7 days restores NO homeostasis and protects the heart from ischemia/reperfusion injury (Bryan, N. S., J. W. Calvert, et al. (2007). "Dietary nitrite supplementation protects against myocardial ischemia-reperfusion injury." Proc Natl Acad Sci U S A, vol. 104 no. 48 19144-19149, hereby incorporated by reference herein) providing the first proof of concept that nitrite can be chronically administered and have a profound effect on outcome from heart attack.

Thus, several embodiments of the present invention provide a method for prolonging the half life of nitrate and extending therapeutic benefit. In one embodiment, the method comprises providing a nitrite salt, wherein the nitrite salt is provided in an amount ranging from about 10 mg to about 100 mg; providing a nitrate salt, wherein the nitrate salt is provided in an amount ranging from about 50 mg to about 500 mg; and providing an ascorbic acid, wherein the ascorbic acid is provided in an amount ranging from about 100 mg to about 2000 mg. The nitrate salt and ascorbic acid are administered in combination with the nitrite salt. The nitrite salt and the nitrate salt convert to nitrite in vivo. The ascorbic acid reduces the conversion of nitrite into N-nitroso compounds in vivo, thereby extending the half-life of the nitrite. "Reduces" in this context encompasses, but is not limited to, "minimizes" or "prevents." The ascorbic acid is particularly advantageous in some embodiments because it reduces carcinogens (e.g., N-nitroso compounds) while increasing the bioavailability of nitrite. L-arginine is added in some embodiments. L-arginine, in some embodiments, serves as a substrate for nitric oxide synthase, thereby increasing NO formation, which in turn can increase nitrate and/or nitrite formation. In one embodiment, the nitrite salt, nitrate salt, ascorbic acid, and optionally L-arginine are provide to a mammal in a single dose.

Nitrite in NO Biology

Nitrite has recently been implicated in hypoxic vasodilation in the circulation (Kim-Shapiro, D. B., M. T. Gladwin, et al. (2005). "The reaction between nitrite and hemoglobin: the role of nitrite in hemoglobin-mediated hypoxic vasodilation." *Journal of Inorganic Biochemistry* 99: 237-246). As early as 1880, nitrite was described in terms of its vasodilatory abilities (Reichert, E. T. and S. W. Mitchell (1880). "On the physiological action of potassium nitrite, with a note on the physiological action on man." *Am J Med Sci* 159: 158-180) and much later, Furchgott used acidified sodium nitrite to relax precontracted aortic strips in 1953 (Furchgott, R. F. and S. Bhadrakom (1953). "Reactions of strips of rabbit aorta to epinephrine, isopropylarterenol, sodium nitrite and other drugs." *J Pharcol Exp Ther* 108(2): 129-143). Both studies used supra-physiological concentrations of nitrite. However, recent studies have rediscovered the vasodilatory effect of nitrite on forearm and systemic blood flow after nitrite infusion. Cosby et al. (Cosby, Partovi et al. 2003) suggested that nitrite is a large intravascular storage pool for NO and that nitrite bioactivation to NO could dilate regions with tissue oxygen debt in the human circulation. However, earlier a study by Lauer et al. reported that nitrite lacked intrinsic vasodilatory properties (Lauer, T., M. Preik, et al. (2001). "Plasma nitrite rather than nitrate reflects regional endothelial nitric oxide synthase activity but lacks intrinsic vasodilator action." *Proc Natl Acad Sci USA* 98(22): 12814-12819). This discrepancy is likely due to kinetics and duration of infusion. Nitrite is found in high abundance throughout the mammalian organ system (Bryan, Rassaf et al. 2004). It is normally a short-lived, highly regulated ion in the circulation (200-600 nM) with a half life in whole blood of 110 seconds (Kelm, M. (1999). "Nitric oxide metabolism and breakdown." *Biochim Biophys Acta* 1411: 273-289). Two independent groups have recently demonstrated the cytoprotective effects of nitrite in ischemia-reperfusion injury (Webb, Bond et al. 2004; Duranski, Greer et al. 2005). Duranski et al attribute nitrite's protective effects to the reduction of nitrite to NO by the reductase activity of hemoglobin. The study by Webb et al using an isolated heart setup was in the absence of blood, clearly demonstrating that the myocardial tissue itself can metabolize nitrite without the need for hemoglobin. Moreover, inhalation of nitrite selectively dilates the pulmonary circulation under hypoxic conditions in vivo in sheep (Hunter, C. J., A. Dejam, et al. (2004). "Inhaled nebulized nitrite is a hypoxia-sensitive NO-dependent selective pulmonary vasodilator." *Nat Med* 10: 1122-1127). Experiments in primates revealed a beneficial effect of long-term application of nitrite on cerebral vasospasm (Pluta, Dejam et al. 2005). Topical application of nitrite improves skin infections and ulcerations (Hardwick, J. B., A. T. Tucker, et al. (2001). "A novel method for the delivery of nitric oxide therapy to the skin of human subjects using a semi-permeable membrane." *Clin Sci (Lond)* 100(4): 395-400). Furthermore, in the stomach, nitrite-derived NO seems to play an important role in host defense (Duncan, C., H. Dougall, et al. (1995). "Chemical generation of nitric oxide in the mouth from the enterosalivary circulation of dietary nitrate." *Nat Med* 1(6): 546-551; Dykhuizen, R. S., R. Frazer, et al. (1996). "Antimicrobial effect of acidified nitrite on gut pathogens: importance of dietary nitrate in host defense." *Antimicrob Agents Chemother* 40(6): 1422-1425) and in regulation of gastric mucosal integrity (Bjorne, H. H., J. Petersson, et al. (2004). "Nitrite in saliva increases gastric mucosal blood flow and mucus thickness." *J Clin Invest* 113 (1): 106-114). All of these studies together along with the observation that nitrite can act as a marker of NOS activity (Kleinbongard, Dejam et al. 2003) opened a new avenue for the diagnostic and therapeutic application of nitrite, especially in cardiovascular diseases, using nitrite as marker as well as an active agent. However, it is still not known how and to what extent nitrite reduction to NO occurs or how the NO-independent effects of nitrite contribute to the cytoprotection of ischemia/reperfusion insult.

The History of Nitrite and Nitrate

Nitrite has clearly emerged as an important molecule in biology, but its effects on the endogenous NO pathway have been poorly investigated. Furthermore, its use as a potential therapy needs further safety consideration. Historically nitrite was considered a strong oxidant and potential carcinogen. It has been in widespread use for many years. It is used as a color fixative and preservation in meats and fish and is naturally occurring in the soil and in vegetables. It is also used in manufacturing diazo dyes, nitroso compounds, in the textile industry, in photography and in the manufacture of rubber chemicals. Nitrite is also a common clinical and laboratory chemical that is used as a vasodilator (Reichert and Mitchell 1880), bronchodilator (Hunter, Dejam et al. 2004), intestinal relaxant (Kozlov, A. V., B. Sobhian, et al. (2001). "Organ specific formation of nitrosyl complexes under intestinal ischemia-reperfusion in rats involves NOS-independent mechanism(s)." *Shock* 15: 366-371) and used as an antidote for cyanide poisoning (Chen, K. K. and C. L. Rose (1952). "Nitrite and thiosulfate therapy in cyanide poisoning." *J Am Med Assoc* 149(2): 113-119). Considering its widespread use there have been many toxicological studies on acute and chronic exposure to nitrite. The fatal dose of nitrite is in the range of 22-23 mg/kg body weight (from USFDA Generally Recognized as Safe Food Ingredient: Nitrates and Nitrites (Including Nitrosamines) 1972 by Battele-Columbus Laboratories and Department of Commence, Springfield Va.). Lower doses of either nitrite or nitrate have caused acute methemoglobinemia, particularly in infants. In infants, a high nitrite or nitrate intake has been associated with "blue baby syndrome" caused by methemoglobinemia (Comly, H. H. (1945). "Cyanosis in infants caused by nitrates in well water." *JAMA* 129: 112-116; Donohoe, W. E. (1949). "Cyanosis in infants with drinking water as a cause." *Paediatrics* 3: 308-311; Lecks, H. I. (1950). "Methemoglobinemia in infancy." *Am J Dis Child* 79: 117-123). The major public health concern, particularly in the 1970s, was the endogenous formation of N-nitrosamines from nitrite and nitrate and its relevance to human cancer. The first report in the 1950s on the hepatocarcinogenic effects of N-nitrosodimethylamine (NDMA) (Magee, P. H. and J. M. Barnes (1956). "The production of malignant primary heptic tumors in the rat by feeding dimethylnitrosamine." *Br. J. Cancer* 10: 114-122), and the suggestion that low molecular weight N-nitrosamines (RNNO) can be formed following nitrosation of various amines (Druckrey, H. and R. Preussmann (1962b). "Die Bilding carcinogener Nitrosamine am Beispiel des Tabakrauchs." *Naturewissenschaften* 49: 498-499) ignited an enormous interest in N-nitrosamines and their association with cancer. Direct proof that such nitrosation reactions can occur was provided by Ender et al. (Ender, F., C. Havre, et al. (1964). "Isolation and identification of a hepatotoxic factor in herring meat produced from sodium nitrite preserved herring." *Naturwissenschaften* 51: 637-638) who identified NDMA in nitrite preserved fish, and by Sander and Sief (Sander, J. and F. Seif (1969). "Bakterielle Reduction von nitrat im magen des menschen als ursache einer Nitrosamin-Bildung." *Arzneimittel-Forsch* 19: 1091-1093) who demonstrated the in vivo formation of a nitrosamine in the acidic conditions of the human stomach. Because of the potent carcinogenicity, wide environmental occurrence and ease of formation of nitrosamines, considerable effort has been made to determine the levels of nitrite and nitrate in the external and internal human environment, and to assess exposure in order to correlate it with human cancer at specific sites (Bartsch, H. and R. Montesano (1984). "Relevance of nitrosamines to human cancer." *Carcinogenesis* 5(11): 1381-1393). Since the early 1980s there have been numerous reports on the association of N-nitrosamines and human cancers (Craddock, V. M. (1983). "Nitrosamines and human cancer: proof of an association?" *Nature* 306: 638; Bartsch and Montesano 1984) but a causative link between nitrite exposure and cancer is still missing (Ward, M. H., T. M. deKok, et al. (2005). "Workgroup report: Drinking-water nitrate and health—recent findings and research needs." *Environ Health Perspect* 113(11): 1607-14). Furthermore, a two year study on the carcinogenicity of nitrite by NIH has conclusively found that there was no evidence of carcinogenic activity by sodium nitrite in male or female rats or mice (Program, N. T. (2001). On The Toxicology and Carcinogenesis Studues of Sodium Nitrite. U. S. D. o. H. a. H. Services, National Institute of Health. NTP TR 495: 1-276). These negative connotations of nitrite and nitrate have led the United States government to regulate and restrict the levels in food and drinking water. Early studies on nitrogen balance in humans and analyses of fecal and ileostomy samples indicated that nitrite and nitrate are formed de novo in the intestine. It was these early findings by Tannenbaum et al. (Tannenbaum, S. R., D. Fett, et al. (1978). "Nitrite and nitrate are formed by endogenous synthesis in the human intestine." *Science* 200: 1487-1488) that significantly altered conceptions of human exposure to exogenous nitrite and nitrates and represented the original observations that would eventually lead to the discovery of the L-argininine:NO pathway. Prior to these studies it was thought that steady-state levels of nitrite and nitrate originated solely from the diet and from nitrogen-fixing enteric bacteria. Endogenous sources of nitrite in mammals are derived from: 1. oxidation of endogenous nitric oxide, 2. nutritional sources such as meat, vegetable and drinking water, 3. reduction of salivary nitrate by commensal bacteria in the mouth and gastrointestinal tract. The discovery of the NO pathway and the emerging biomedical applications of nitrite and nitrate necessitate a paradigm shift on the role of nitrite and nitrate in physiology.

Nitrate/Nitrite Reduction to NO

Humans, unlike prokaryotes, are thought to lack the enzymatic machinery to reduce nitrate back to nitrite. However, due to the commensal bacteria that reside within the human body it has been demonstrated that these bacteria can reduce nitrate thereby supplying an alternative source of nitrite (Goaz, P. W. and H. A. Biswell (1961). "Nitrite reduction in whole saliva." *J Dent Res* 40: 355-365; Tannenbaum, Sinskey et al. 1974; Ishiwata, H., A. Tanimura, et al. (1975). "Nitrite and nitrate concentrations in human saliva collected from salivary ducts." *J Food Hyg Soc Jpn* 16: 89-92; van Maanen, van Geel et al. 1996). Therefore dietary and enzymatic sources of nitrate are now a potentially large source of nitrite in the human body. Nitrate is rapidly absorbed in the small intestines and readily distributed throughout the body (Walker, R. (1996). "The metabolism of dietary nitrites and nitrates." *Biochem Soc Trans* 24(3): 780-785). As much as 25% of the ingested nitrate is actively taken up by the salivary glands to be excreted in the saliva (Spiegelhalder, B., G. Eisenbrand, et al. (1976). "Influence of dietary nitrate on nitrite content of human saliva: possible relevance to in vivo formation of N-nitroso compounds." *Food Cosmet Toxicol* 14: 545-548). Approximately 20% of the salivary nitrate is then reduced to nitrite by bacteria in the mouth (Spiegelhalder, Eisenbrand et al. 1976) and then disproportionates with formation of NO after entering the acidic environment of the stomach. This nitrate pathway to NO has been shown to help reduce gastrointestinal tract infection, increase mucous barrier thickness and gastric blood flow (Pique, J. M., B. J. Whittle, et al. (1989). "The vasodilator role of endogenous nitric oxide in the rat gastric microcirculation." *Eur. J. Pharmacol* 174(2-3): 293-296; Brown, J. F., P. J. Hanson, et al. (1992). "Nitric oxide donors increase mucus gel thickness in rat stomach." *Eur. J. Pharmacol* 223(1): 103-104; McKnight, G. M., L. M. Smith, et al. (1994). "Chemical synthesis of nitric oxide in the stomach from dietary nitrate in humans." *Gut* 40(2): 211-214; Walker 1996). The concentrations of nitrate in drinking water are usually <10 mg/L in the absence of bacterial contamination (Kross, B. C., G. R. Hallberg, et al. (1993). "The nitrate concentration of private well water in Iowa." *Am J Public Health* 83(2): 270-272). Vegetables, especially beets, celery, and leafy vegetables like lettuce and spinach are rich in nitrates (Meah, M. N., N. Harrison, et al. (1994). "Nitrate and nitrite in foods and the diet." *Food Addit Contam* 11(4): 519-532; Walker 1996; Vallance, P. (1997). "Dietary nitrate: poison or panacea?" *Gut* 40(2): 211-214). Other vegetables contain nitrate at lower concentrations, but because they are consumed in greater quantity, they may contribute more nitrate and thus nitrite from the diet. For the average population, most nitrate exposure (86%) comes from vegetables, whereas the primary contributors to nitrite intake are cured meats (39%), baked goods and cereals (34%), and vegetables (16%). The National Research Council report *The Health Effects of Nitrate, Nitrite, and N-Nitroso Compounds* (NRC 1981) reported estimates of nitrite and nitrate intake based on food consumption tables. They report that the average total nitrite and nitrate intake in the U.S. was 0.77 mg and 76 mg, respectively per day. Nitrite and nitrate are excreted in the kidneys. Nitrate is excreted in the urine as such or after conversion to urea (Green, L. C., K. Ruiz de Luzuriaga, et al. (1981). "Nitrate biosynthesis in man." *Proc. Natl. Acad Sci. USA* 78(12): 7764-7768). Clearance of nitrate from blood to urine approximates 20 ml/min in adults (Wennmalm, A., G. Benthin, et al. (1993). "Metabolism and excretion of nitric oxide in humans. An experimental and clinical study." *Circ Res* 73(6): 1121-1127), indicating considerable renal tubular reabsorption of this ion. There is little detectable nitrite or nitrate in feces (Bednar, C. and C. Kies (1994). "Nitrate and Vitamin C from fruits and vegetables: impact of intake variations on nitrate and nitrite excretions in humans." *Plant Foods Hum Nutr* 45(1): 71-80). There is some loss of nitrate and nitrite in sweat, but is not a major route of excretion (Weller, R., S. Pattullo, et al. (1996). "Nitric oxide is generated on the skin surface by reduction of sweat nitrate." *J Invest Dermatol* 107(3): 327-331). Assuming the human body (70 kg) produces 1.68 mmole NO per day (based on 1 µmole/kg/hr NO production), an average daily intake of 0.77 mg of nitrite would equate to 11.1 µmoles per day and 76 mg nitrate would equate to 894 µmoles per day or roughly 1 mmole NOx per day from diet. This almost matches what the human body makes from NO, assuming most of the NO goes to stepwise oxidation to nitrite and nitrate.

Nitrite Physiology

The endogenous production of NO by NOS has been established as playing an important role in vascular homeostasis, neurotransmission, and host defense mechanisms (Moncada, S., R. M. J. Palmer, et al. (1991). "Nitric oxide: physiology, pathophysiology and pharmacology." *Pharmacol Rev* 43(2): 109-142). The major pathway for NO metabolism is the stepwise oxidation to nitrite and nitrate (Yoshida, K., K. Kasama, et al. (1983). "Biotransformation of nitric oxide, nitrite and nitrate." *Int Arch Occup Environ Health* 52: 103-115). In plasma or other physiological fluids or buffers, NO is oxidized almost completely to nitrite, where it remains stable for several hours (Kelm, M., M. Feelisch, et al. (1992). The Biology of nitric oxide. Physiological and Clinical Aspects. S. Moncada, M. A. Marletta, J. B. Hibbs and E. A. Higgs. London, Portland Press. 1: 319-322, hereby incorporated by reference herein; Grube, R., M. Kelm, et al. (1994). The Biology of Nitric Oxide. *Enzymology, Biochemistry, and Immunology*. S. Moncada, M. Feelisch, R. Busse and E. A. Higgs. London, Portland Press. 4: 201-204, hereby incorporated by reference herein); however, the half life of $NO_2^-$ in human whole blood is about 110 seconds (Kelm 1999).

The oxidation of NO by molecular oxygen is second order with respect to NO:

$$2NO + O_2 \rightarrow 2NO_2 \quad (1)$$

$$2NO + 2NO_2 \rightarrow 2N_2O_3 \quad (2)$$

$$2N_2O_3 + 2H_2O \rightarrow 4NO_2^- + 4H^+ \quad (3)$$

whereby $NO_2$, $N_2O_3$ and $NO_2^-$ represent nitrogen dioxide, dinitrogen trioxide and nitrite, respectively. It should be noted that $N_2O_3$ is a potent nitrosating agent by virtue of its ability to generate the nitrosonium ion ($NO^+$). NO and nitrite are rapidly oxidized to nitrate in whole blood. As stated above, the half life of $NO_2^-$ in human blood is about 110 seconds (Kelm 1999). Nitrate on the other hand has a circulating half life of 5-8 hours (Tannenbaum, S. R. (1994). "Nitrate and nitrite: origin in humans." *Science* 205: 1333-1335, hereby incorporated by reference herein; Kelm, M. and K. Yoshida (1996). Metabolic Fate of Nitric Oxide and Related N-oxides. *Methods in Nitric Oxide Research*. M. Feelisch and J. S. Stamler. Chichester, John Wiley and Sons: 47-58, hereby incorporated by reference herein). Although the mechanisms by which NO and $NO_2^-$ are converted to $NO_3^-$ in vivo are not entirely clear, there are several possibilities. During fasting conditions with low intake of nitrite/nitrate, enzymatic NO formation from NOS accounts for the majority of nitrite (Rhodes, P., A. M. Leone, et al. (1995). "The L-arginine:nitric oxide pathway is the major source of plasma nitrite in fasted humans." *Biochem Biophys Res Commun* 209: 590-596).

NO production from nitrite has been described in infarcted heart tissue (Zweier, J. L., et al., *Enzyme-independent formation of nitric oxide in biological tissues*. Nature Medicine, 1995. 1(8): p. 804-809). Nitrite reductase activity in mammalian tissues has been linked to the mitochondrial electron transport system (Walters, C. L., R. J. Casselden, and A. M. Taylor, *Nitrite metabolism by skeletal muscle mitochondria in relation to haem pigments*. Biochim Biophys Acta, 1967. 143: p. 310-318; Reutov, V. P. and E. G. Sorokina, *NO-synthase and nitrite-reductase components of nitric oxide cycle*. Biochemistry (Mosc), 1998. 63(7): p. 874-884; Kozlov, A. V., K. Staniek, and H. Nohl, *Nitrite reductase activity is a novel function of mammalian mitochondria*. FEBS Lett, 1999. 454: p. 127-130; Nohl, H., et al., *Mitochondria recycle nitrite back to the bioregulator nitric monoxide*. Acta Biochim Pol, 2000. 47: p. 913-921; Tischner, R., E. Planchet, and W. M. Kaiser, *Mitochondrial electron transport as a source for nitric oxide in the unicellular green algae Chlorella sorokiniana*. FEBS Lett, 2004. 576: p. 151-155), protonation (Zweier, J. L., et al., *Enzyme-independent formation of nitric oxide in biological tissues*. Nature Medicine, 1995. 1(8): p. 804-809; Hunter, C. J., et al., *Inhaled nebulized nitrite is a hypoxia-sensitive NO-dependent selective pulmonary vasodilator*. Nat Med, 2004. 10: p. 1122-1127), deoxyhemoglobin (Hunter, C. J., et al., *Inhaled nebulized nitrite is a hypoxia-sensitive NO-dependent selective pulmonary vasodilator*. Nat Med, 2004. 10: p. 1122-1127; Cosby, K., et al., *Nitrite reduction to nitric oxide by deoxyhemoglobin vasodilates the human circulation*. Nature Medicine, 2003. 9: p. 1498-1505), and xanthine oxidase (Li, H., et al., *Characterization of the effects of oxygen on xanthine oxidase-mediated nitric oxide formation*. J. Biol Chem, 2004. 279: p. 16939-16946; Alikulov, Z. A., N. P. L'vov, and V. L. Kretovich, *Nitrate and nitrite reductase activity of milk xanthine oxidase*. Biokhimiia, 1980. 45(9): p. 1714-1718; Webb, A., et al., *Reduction of nitrite to nitric oxide during ischemia protects against myocardial ischemia-reperfusion damage*. Proc Natl Acad Sci USA, 2004. 101(13683-13688)). Mitochondrial nitrite reduction has been shown to occur by ubiquinol (Kozlov, A. V., K. Staniek, and H. Nohl, *Nitrite reductase activity is a novel function of mammalian mitochondria*. FEBS Lett, 1999. 454: p. 127-130; Nohl, H., et al., *The multiple functions of coenzyme Q*. Bioorg Chem, 2001. 29(1): p. 1-13) and cytochrome c oxidase (Castello, P. R., et al., *Mitochondrial cytochrome oxidase produces nitric oxide under hypoxic conditions: implications for oxygen sensing and hypoxic signaling in eukaryotes*. Cell Metab, 2006. 3(4): p. 277-87) with subsequent binding of the NO produced to cytochrome bc1 site of complex III or complex IV resulting in oxygen-dependent reversible inhibition of mitochondrial respiration (Takehara, Y., et al., *Oxygen-dependent reversible inhibition of mitochondrial respiration by nitric oxide*. Cell Struct Funct, 1996. 21(4): p. 251-8). The acidic reduction of nitrite requires protonation and a one-electron reduction. The relatively low pKa of nitrite (3.34) (*Principles of Modern Chemistry*. Third ed, ed. D. W. Oxtoby and N. H. Nachtrieb. 1996, Fort Worth: Harcourt Brace College Publishers. 848) limits this activity in physiology but it can occur in the stomach or during ischemic events when tissue pH falls. Since many different pathways have been shown to be able to reduce nitrite but require different conditions and substrates for optimal nitrite reduction, it is likely that all pathways may become relevant but at different oxygen tension, substrate availability, and perhaps even compartment specific needs.

The evolution of nitrite from a vilified substance that generates carcinogenic nitrosamines in the stomach, to a lifesaving drug that liberates a protective agent (NO) during hypoxic events, as well as performs many actions independent of NO, warrants a re-evaluation of nitrite in biology. With nitrite acting as both an end product of NO synthesis and a reservoir for NO, it is therefore a critical homeostatic molecule in NO biology.

The collective evidence reviewed in this section strongly supports the notion that there is a fundamental and physiological basis for developing nitrite-based therapeutics. It is not understood how orally ingested nitrite (pKa 3.8) can survive the acidic environment of the stomach (pH 1-2). Furthermore, once nitrite is absorbed into the bloodstream it is known to be quickly oxidized to nitrate with a half life of 110 seconds. Surprisingly, several embodiments of the present invention demonstrate that orally administered nitrite in specific combination with nitrate and ascorbic acid can extend the therapeutic range of nitrite from seconds to tens of minutes providing a novel approach to treat or reduce injury from heart attack with nitrite. In some embodiments ascorbic acid reduces endogenous nitrosation reaction in the gastrointestinal tract, which enhances the half life of nitrite. In some embodiments, the nitrate provides an additional source of nitrite, again extending the functional half life, e.g., by increasing stores, of nitrite.

The human diet exerts important long-term effects on vital body functions and thereby makes an important contribution to health and disease. While high intake of cholesterol, saturated fat, salt, and sugar are associated with a greater risk for cardiovascular disease, conventional wisdom has it that the opposite is true for abundant consumption of fruits and vegetables. A diet rich in fruits and vegetables is associated with a lower risk of certain forms of cancer and cardiovascular disease. Recent epidemiological studies suggest a cardioprotective action afforded specifically by green leafy vegetables. Green leafy vegetables such as spinach and lettuce, in addition to being rich in antioxidants are especially rich in nitrite and nitrate as are berries, grapes, and a few other fruits. The high content of nitrite and nitrate is a major factor contributing to the positive health effects of certain vegetables via bioconversion to NO which exerts protective effects on the cardiovascular system. A continuous intake of nitrite- and nitrate-containing food such as green leafy vegetables and berries may ensure that blood and tissue levels of NO are maintained at a level sufficient to compensate for any disturbances in endogenous NO synthesis. Dietary source of NO metabolites could therefore improve circulation and oxygen delivery and lead to better health and increased energy. This dietary pathway may therefore not only provide essential nutrients for NO production but also provide a rescue pathway for people at risk for cardiovascular disease. Several embodiments provide the nutrition and protection of a high vegetable diet in the form of a daily supplement formulation which renders subjects protected from injury from heart attack or other cardiovascular events, i.e. stroke, pulmonary embolism. This strategy including nitrite/nitrate supplementation in combination with ascorbic acid may serve as an inexpensive cardioprotective regimen which may delay or reduce the onset or progression of cardiovascular or heart disease and protect from myocardial infarction.

Several embodiments of the invention are particularly advantageous because they provide a supplement formulation of nitrite, nitrate and Vitamin C. Although, in some embodiments, such amounts may be found in a high vegetable diet, the time it would take to consume the required assortment of vegetables as well as the impact on the digestive system would adversely impact the absorption and/or bioavailability of the nitrite, nitrate and Vitamin C. Moreover, the reaction of other compounds and nutrients in the naturally occurring vegetable assortment may also adversely impact the impact the absorption and/or bioavailability of the nitrite, nitrate and Vitamin C. Thus, a supplement of nitrite, nitrate and Vitamin C in e.g., daily dose formulations are advantageous in several embodiments because it increases the absorption and/or bioavailability of the formulation. In some embodiments, the formulation comprises purified or isolated nitrite, nitrate and Vitamin C. In other embodiments, the formulation consists essentially of purified or isolated nitrite, nitrate and Vitamin C. In yet other embodiments, the formulation consists of purified or isolated nitrite, nitrate and Vitamin C.

In other embodiments, the formulation consists essentially of purified or isolated nitrite, nitrate, Vitamin C, and L-arginine. In yet other embodiments, the formulation consists of purified or isolated nitrite, nitrate, Vitamin C, and L-arginine.

In one embodiment, "consists essentially of" means the composition may further contain one or more components selected from the group consisting of water and flavorants.

With 1 in every 3 men and 1 in every 10 women in the U.S. expected to develop some major cardiovascular disease before reaching age 60 is it desirable to take preventive measures now to enhance cardiovascular health.

In one embodiment, the present invention can provide a novel therapy for patients experiencing myocardial infarction or stroke. Nitrite has been shown to be protective in animal models of stroke and both cardiac and hepatic ischemia-reperfusion injury. Conversely, nitrite insufficiency is associated with increased injury from ischemia-reperfusion insult. However, because of the short half-life of nitrite in the circulation (110 sec), the therapeutic window for nitrite alone is very narrow. Therefore, several embodiments provide patients with an extended-release formulation comprising nitrite, among additional components, to be used upon onset of symptoms to provide at least some protection from injury until the patient can be provided with reperfusion therapy, such as in a hospital setting.

In several embodiments, the present invention relates to the use of supplemental nitrite in combination with nitrate and vitamin C (ascorbic acid) as a preventive agent in cardiovascular disease. In some embodiments nitrate acts as an extended release nitrite source that is absorbed and re-circulated through the enterosalivary pathway and is reduced to nitrite by commensal bacteria in the mouth. In some embodiments nitrite acts as a reservoir for nitric oxide activity. Reduced nitric oxide availability is a hallmark of a number of cardiovascular disorders and plasma nitrite levels progressively decrease with increasing cardiovascular risk load. Therefore, several embodiments provide a sufficient daily intake of nitrite, which is beneficial to optimal cardiovascular health. A typical Western diet is low in nitrite and nitrate compared to a vegetarian or Mediterranean diet and may therefore account for the increased incidence of cardiovascular disease in the United States, Europe, and other developed countries. A daily nitrite supplementation may provide the missing nutrient, analogously to a daily multivitamin. The Nobel Prize in Physiology or Medicine was awarded in 1998 for the discovery of nitric oxide in the cardiovascular system. Maintaining nitric oxide availability is essential for optimal health, particularly for those at risk for cardiovascular events, and therefore, in several embodiments, supplemental nitrite acts to increase the reservoir of nitric oxide which can be bio-activated upon need as a prevention rather than a treatment or therapy once disease has occurred.

In one embodiment, the present invention relates to a formulation for an alternate source of nitric oxide during cardiovascular exercise and/or muscle training. In a further embodiment, the formulation further comprises L-arginine. L-arginine is a natural amino acid substrate for nitric oxide synthase enzymes which produces L-citrulline and NO from L-arginine in a complex reaction requiring oxygen. L-arginine can be given as a pre-workout drink to saturate the NOS enzyme to produce sufficient NO and dilate vessels. However, under conditions where muscles are working during anaerobic metabolism, oxygen availability is diminished and therefore NOS can no longer produce NO. Therefore an alternate substrate must be supplied to produce NO under anaerobic conditions. The substrate then becomes nitrite. Several embodiments supply blood and muscles with nitrite before a workout, which provides an additional source of NO during the workout and improves muscle blood flow during exercise, thereby enhancing performance and muscle building capacity. In one embodiment, sodium nitrite is added to existing workout beverage formulations, thereby increasing NO and providing sufficient NO before during and/or after a workout. Since the L-arginine:NO pathway is not functional during workout, the addition of nitrite provides the substrate for anaerobic formation of NO, an alternate pathway for NO generation. So instead of increasing NO production before and after a workout through the L-arginine:NO pathway, the presence of nitrite in certain embodiments of the formulation will allow NO production from nitrite reduction during the workout, a time at which it is advantageous to increase blood flow and supply the muscles with essential nutrients and oxygen.

In one embodiment, the present invention relates to a composition comprising a nitrite salt, a nitrate salt, and ascorbic acid.

Any positively-charged ion safe for use as a food additive or a component of a pharmaceutical formulation can be used as the counterion to nitrite in the nitrite salt or the counterion to nitrate in the nitrate salt. In one embodiment, the positively-charged ion is an inorganic ion. In a further embodiment, the positively-charged ion is selected from the group consisting of sodium and potassium; e.g., the nitrite salt is sodium nitrite or potassium nitrite and the nitrate salt is sodium nitrate or potassium nitrate.

Any proportions of the components of the composition can be used. In one embodiment, the composition comprises from about 1 weight part to about 8 weight parts sodium nitrite, from about 5 weight parts to about 50 weight parts sodium nitrate, and from about 20 weight parts to about 200 weight parts ascorbic acid.

In one embodiment, the composition further comprises L-arginine. In a further embodiment, the composition comprises from about 20 weight parts to about 200 weight parts L-arginine.

In some embodiments, sodium nitrite is included in a range of about 0.01 mg/kg to about 15 mg/kg. In some embodiments, sodium nitrate is included in a range of about 1.0 mg/kg to about 50 mg/kg. In some embodiments, ascorbic acid is included in a range of about 1.0 mg/kg to about 25 mg/kg. In certain embodiments, L-arginine may also be included in a range of about 2.0 mg/kg to about 50 mg/kg.

In certain embodiments that enhance NO formation in working muscle, sodium nitrite is included in a range of about 30 mg to about 40 mg. In certain embodiments, sodium nitrate is included in a range of about 250 mg to about 300 mg. In certain such embodiments, ascorbic acid is included in an amount of about 1000 mg. In certain other embodiments, L-arginine may also be included in an amount of about 1000 mg.

In certain embodiments that function to restore NO homeostasis in the user, sodium nitrite is included in an amount of about 20 mg. In certain such embodiments, sodium nitrate is included in an amount of about 150 mg. In certain embodiments, ascorbic acid is included in an amount of about 500 mg. In certain other embodiments, L-arginine may also be included in an amount of about 500 mg.

The composition can further comprise other materials. In one embodiment, the composition further comprises water. Alternatively or in addition, it can also further comprise other materials. For example, the composition may comprise a flavorant, such as a citrus flavor, a non-citrus fruit flavor, an herbal flavor, a vanilla flavor, or a chocolate flavor, and other appropriate flavorings.

In other embodiments, the present invention relates to a method of enhancing cardiovascular performance in a mammal, comprising administering to the mammal a composition according to any of the embodiments described herein. In one embodiment, the composition comprises a nitrate salt, a nitrate salt, and ascorbic acid.

Any mammal for which enhanced cardiovascular performance is desired can be the subject of the method. In one embodiment, the mammal is *Homo sapiens*. Other mammals for which enhanced cardiovascular performance may be desired include, but are not limited to, draft animals, beasts of burden, animals useful in transportation (e.g., horses), racing animals (e.g., horses or greyhounds), meat animals, wool- or fur-bearing animals, milk animals, working dogs, and household pets, among others. Enhanced cardiovascular performance can be desired for a person or animal engaged in physical exertion. In other embodiments, a composition as described herein may be used as a treatment or prophylaxis for a medical condition characterized by or associated with reduced blood flow to an organ of the body.

Administering the composition can be by any route, such as oral, intravenous, or intraarterial, among others. In one embodiment, administering is by the oral route. In this embodiment, it is desirable that the components of the composition be dissolved in a neutral- or pleasant-tasting liquid, such as water, flavored water, milk, or fruit juice, among others. Additionally, the components of the composition may be in tablet or capsule form and in this form the composition may be dissolvable in liquid. In other embodiments, the composition is provided as a tablet that dissolves when placed in the mouth of a user. In some embodiments, a composition according to any of the embodiments described herein can be provided in powder, tablet, capsule, gel, aerosol or liquid form.

Any dosage of the components of the composition can be used, provided such dosage is safe for the mammal. In one embodiment, administering is of a dosage from about 0.01 mg/kg/day to about 15 mg/kg/day sodium nitrite, from about 1 mg/kg/day to about 50 mg/kg/day sodium nitrate, and from about 1 mg/kg/day to about 25 mg/kg/day ascorbic acid. If the composition comprises L-arginine, administering is of a dosage from about 2 mg/kg/day to about 50 mg/kg/day L-arginine.

In one embodiment, the present invention is directed to a composition, comprising from about 40 weight parts to about 1000 weight parts of a botanical nitrate source; from about 20 weight parts to about 500 weight parts of a botanical source of nitrite reduction activity; and from about 4 weight parts to about 100 weight parts of a nitrite salt.

A botanical nitrate source is any plant matter, extract of plant matter, or product of plant matter containing nitrate. Generally, it is desirable that the botanical nitrate source be generally regarded as safe for human or animal consumption. In one embodiment, the botanical nitrate source is selected from the group consisting of beet root, artichoke, holy basil, gymnema sylvestre, L9H, ashwagandha root, salvia, St. John wort, broccoli, stevia, spinach, gingko, kelp, tribulus, eleuthero, epimedium, eucommia, hawthorn berry, rhodiola, green tea, codonopsys, panax ginseng, astragalus, pine bark, dodder seed, *Schisandra*, cordyceps, and mixtures thereof. In one particular embodiment, the botanical nitrate source is selected from the group consisting of beet root, artichoke, holy basil, gingko, and mixtures thereof A botanical source of nitrite reduction activity is any plant matter, extract of plant matter, or product of plant matter, containing nitrite reductase enzyme, a compound capable of reducing nitrite, or both. Generally, it is desirable that the botanical source of nitrite reduction activity be generally regarded as safe for human or animal consumption. In one embodiment, the botanical source of nitrite reduction activity is selected from the group consisting of hawthorn berry, *Schisandra*, green tea, beet root, pine bark, holy basil, gymnema sylvestre, L9H, ashwagandha root, salvia, St. John wort, broccoli, stevia, spinach, gingko, kelp, tribulus, eleuthero, epimedium, eucommia, rhodiola, green tea, codonopsys, panax ginseng, astragalus, dodder seed, cordyceps, berries, tea, beer, grapes, wine, olive oil, chocolate, cocoa, coffee, walnuts, peanuts, borojo, pomegranates, popcorn, yerba mate, and mixtures thereof. Berries, tea, beer, grapes, wine, olive oil, chocolate, cocoa, coffee, walnuts, peanuts, borojo, pomegranates, popcorn, and yerba mate are known to contain polyphenols, which are known to have antioxidant properties.

In a particular embodiment, the botanical source of nitrite reduction activity is selected from the group consisting of hawthorn berry, *Schisandra*, green tea, beet root, pine bark, and mixtures thereof.

"Hawthorn berry" herein refers to any portion of a plant of the genus *Crataegus* (for example, *Crataegus oxyacantha*), such as the berry, leaf, or flower, among others, as well as extracts of any portion thereof. In a particular embodiment, it refers to the berry of a plant of the genus *Crataegus* (for example, *Crataegus oxyacantha*).

"*Schisandra*" refers to any portion of a plant of the genus *Schisandra* (for example, *S. chinensis* and *S. rubiflora*, among others), such as the fruit, leaf, or flower, among others, as well as extracts of any portion thereof.

A nitrite salt comprising any counterion may be used. Generally, it is desirable that the nitrite salt be generally regarded as safe for human or animal consumption. In one embodiment, the nitrite salt is selected from the group consisting of sodium nitrite, potassium nitrite, magnesium nitrite, calcium nitrite, and mixtures thereof. In a particular embodiment, the nitrite salt is selected from the group consisting of sodium nitrite, potassium nitrite, and mixtures thereof In addition to the materials described above, the composition can further comprise one or more additional materials.

In one embodiment, the composition can further comprise from about 20 weight parts to about 500 weight parts L-citrulline.

In one embodiment, the composition can further comprise from about 20 weight parts to about 1000 weight parts L-arginine.

The production of NO from L-arginine is a critical cellular function performed by nitric oxide synthase (NOS) in most, if not all, organ systems throughout the body. For years, physicians and scientists assumed simply feeding more substrate L-arginine would be sufficient to enhance NO production. It is becoming increasingly clear that this may not be the most effective strategy, especially in patients that are insufficient in NO due to endothelial dysfunction. The effect of L-arginine on endothelial function in humans is inconsistent. By definition endothelial dysfunction is the inability to produce NO from L-arginine. This pathway is dysfunctional and inoperative. Providing the enzyme NOS with substrate because of lowered availability of L-arginine does not appear to be rate limiting since the intracellular levels of the amino acid are in the millimolar range (Gold, M. E., P. A. Bush, and L. J. Ignarro, *Depletion of arterial L-arginine causes reversible tolerance to endothelium-dependent relaxation*. Biochem Biophys Res Commun, 1989. 164(2): p. 714-21), and the enzyme's Michaelis constanst ($K_M$) for substrate is in the micromolar range (2.9 µmol/L) (Bredt, D. S. and S. H. Snyder, *Isolation of nitric oxide synthetase, a calmodulin-requiring enzyme*. Proc Natl Acad Sci U S A, 1990. 87(2): p. 682-5). In contrast, circulating L-arginine measured in plasma of healthy humans as well as in plasma of patients with vascular disorders is in the range of 45-100 µmol/L (Boger, R. H. and S. M. Bode-Boger, *The clinical pharmacology of L-arginine*. Annu Rev Pharmacol Toxicol, 2001. 41: p. 79-99). This is up to 15 to 30-fold higher than the concentration required to saturate the NOS enzyme. This biochemical discrepancy is termed as the "arginine paradox."

L-Arginine supplementation may be detrimental in some populations. A clinical trial designed to enhance NO production in humans that have suffered a heart attack revealed that L-arginine, when added to standard postinfarction therapies, does not improve vascular stiffness measurements or ejection fraction and may be associated with higher postinfarction mortality. The study concluded that L-arginine should not be recommended following acute myocardial infarction (Schulman, S. P., et al., *L-arginine therapy in acute myocardial infarction: the Vascular Interaction With Age in Myocardial Infarction (VINTAGE MI) randomized clinical trial*. Jama, 2006. 295(1): p. 58-64).

The vast majority of endogenous arginine synthesis in adult mammals (60%) occurs in the kidney, where citrulline produced by the intestine is extracted from the blood and converted to arginine by the action of ASS and ASL (Windmueller, H. G. and A. E. Spaeth, *Source and fate of circulating citrulline*. Am J Physiol, 1981. 241(6): p. E473-80). Therefore supplying more L-citrulline to the urea cycle will produce more L-arginine to be specifically directed to the nitric oxide pathway; in other words, supplying more L-citrulline provides precursors to the L-arginine nitric oxide pathway while avoiding the negative side effects of supplementing L-arginine directly.

In one embodiment, the composition can further comprise from about 0.2 weight parts to about 5 weight parts vitamin B12. The vitamin B12 can be in any form of cobalamin. In one embodiment, the vitamin B12 is in a form selected from the group consisting of methylcobalamin, cyanocobalamin, and mixtures thereof.

In one embodiment, the composition can further comprise from about 20 weight parts to about 500 weight parts vitamin C. The vitamin C can be in any form of ascorbate or ascorbic acid. In one embodiment, the vitamin C is in a form selected from the group consisting of magnesium ascorbate, sodium ascorbate, potassium ascorbate, ascorbic acid, and mixtures thereof.

In one embodiment, the composition can further comprise from about from about 20 weight parts to about 500 weight parts of a nitrate salt selected from the group consisting of sodium nitrate, potassium nitrate, and mixtures thereof.

In addition to the materials described above, the composition can further comprise one or more additional materials suitable for forming the composition into a vehicle deliverable for human or animal consumption. Such one or more additional materials include, but are not limited to, binders, flavorants, colorants, sweeteners, adujvants, and excipients, among others.

In one embodiment, the composition can further comprise from about 50 weight parts to about 1500 weight parts of one or more other ingredients selected from the group consisting of mannitol, xylitol, sorbitol, other sugar alcohols, cellulose, cellulose esters, cellulose ethers, other modified celluloses, starch, modified starches, other polysaccharides, oligosaccharides, disaccharides, saccharides, gelatin, polyvinylpyrrolidone, polyethylene glycol, other binders, flavorants, colorants, magnesium stearate, other antiadherent agents, other stearate salts, sweeteners, silica, and other lubricants. These one or more ingredients can act as one or more of binders, flavorants, colorants, sweeteners, antiadherents, or lubricants, among other functions.

In one particular embodiment, the composition can be as follows:

the botanical nitrate source is selected from the group consisting of beet root, artichoke, holy basil, gingko, and mixtures thereof and is present at about 200 weight parts;

the botanical source of nitrite reduction activity is selected from the group consisting of hawthorn berry, Schisandra, green tea, beet root, pine bark, and mixtures thereof and is present at about 100 weight parts; and the nitrite salt is selected from the group consisting of sodium nitrite, potassium nitrite, and mixtures thereof and is present at about 20 weight parts;

and the composition further comprises:

about 100 weight parts L-citrulline;

about 1 weight part vitamin B12 in a form selected from the group consisting of methylcobalamin, cyanocobalamin, and mixtures thereof;

about 100 weight parts vitamin C in a form selected from the group consisting of magnesium ascorbate, ascorbic acid, and mixtures thereof; and from about 50 weight parts to about 1500 weight parts of one or more other ingredients selected from the group consisting of mannitol, xylitol, sorbitol, other sugar alcohols, cellulose, cellulose esters, cellulose ethers, other modified celluloses, starch, modified starches, other polysaccharides, oligosaccharides, disaccharides, saccharides, gelatin, polyvinylpyrrolidone, polyethylene glycol, other binders, flavorants, colorants, magnesium stearate, other antiadherent agents, other stearate salts, sweeteners, silica, and other lubricants.

The composition can be formulated, using techniques known in the art, into any vehicle suitable for human consumption. For example, the composition can be formulated as a powder dissolvable or suspendable in a potable beverage, a soft food, or both; as an ingredient that can be baked into a baked cookie, cracker, or bar; a tablet or capsule that can be swallowed; or a lozenge dissolvable in the mouth; among others. In one embodiment, the composition can be in a form of a lozenge dissolvable in the mouth. The lozenge can have a weight from about 600 mg to about 2000 mg.

In one embodiment, the present invention is directed to a method of reducing a patient's triglyceride level, comprising administering to the patient a composition in a form of a lozenge dissolvable in the mouth, the composition comprising from about 40 weight parts to about 1000 weight parts of a botanical nitrate source; from about 20 weight parts to about 500 weight parts of a botanical source of nitrite reduction activity; from about 20 weight parts to about 500 weight parts L-citrulline; and from about 4 weight parts to about 100 weight parts of a nitrite salt.

The composition and its components can be as described above. Also, the formulation of the composition as a lozenge can be as described above.

In one embodiment, 1 weight part is 1 mg.

In a particular embodiment, the administered composition can be as follows:

the botanical nitrate source is selected from the group consisting of beet root, artichoke, holy basil, gingko, and mixtures thereof and is present at about 200 mg;

the botanical source of nitrite reduction activity is selected from the group consisting of hawthorn berry, Schisandra, green tea, beet root, pine bark, and mixtures thereof and is present at about 100 mg; and the nitrite salt is selected from the group consisting of sodium nitrite, potassium nitrite, and mixtures thereof and is present at about 20 mg;

and the composition further comprises:

about 100 mg L-citrulline;

about 1000 µg vitamin B12 in a form selected from the group consisting of methylcobalamin, cyanocobalamin, and mixtures thereof;

about 100 mg vitamin C in a form selected from the group consisting of magnesium ascorbate, ascorbic acid, and mixtures thereof; and from about 50 mg to about 1500 mg of one or more other ingredients selected from the group consisting of mannitol, xylitol, sorbitol, other sugar alcohols, cellulose, cellulose esters, cellulose ethers, other modified celluloses, starch, modified starches, other polysaccharides, oligosaccharides, disaccharides, saccharides, gelatin, polyvinylpyrrolidone, polyethylene glycol, other binders, flavorants, colorants, magnesium stearate, other antiadherent agents, other stearate salts, sweeteners, silica, and other lubricants.

The composition can be administered according to any dosing regimen. Particular details of how administering is to be performed are within the ability of the person of ordinary skill in the art having the benefit of the present disclosure. In one embodiment, the administering is performed once or twice daily.

In one embodiment, the present invention is directed to a method of reducing a patient's C-reactive protein level, comprising administering to the patient a composition in a form of a lozenge dissolvable in the mouth, the composition comprising from about 40 weight parts to about 1000 weight parts of a botanical nitrate source; from about 20 weight parts to about 500 weight parts of a botanical source of nitrite reduction activity; from about 20 weight parts to about 500 weight parts L-citrulline; and from about 4 weight parts to about 100 weight parts of a nitrite salt.

The composition and its components can be as described above. Also, the formulation of the composition as a lozenge can be as described above.

In one embodiment, 1 weight part is 1 mg.

In a particular embodiment, the administered composition can be as follows:

the botanical nitrate source is selected from the group consisting of beet root, artichoke, holy basil, gingko, and mixtures thereof and is present at about 200 mg;

the botanical source of nitrite reduction activity is selected from the group consisting of hawthorn berry, Schisandra, green tea, beet root, pine bark, and mixtures thereof and is present at about 100 mg; and the nitrite salt is selected from the group consisting of sodium nitrite, potassium nitrite, and mixtures thereof and is present at about 20 mg;

and the composition further comprises:

about 100 mg L-citrulline;

about 1000 µg vitamin B12 in a form selected from the group consisting of methylcobalamin, cyanocobalamin, and mixtures thereof;

about 100 mg vitamin C in a form selected from the group consisting of magnesium ascorbate, ascorbic acid, and mixtures thereof; and from about 50 mg to about 1500 mg of one or more other ingredients selected from the group consisting of mannitol, xylitol, sorbitol, other sugar alcohols, cellulose, cellulose esters, cellulose ethers, other modified celluloses, starch, modified starches, other polysaccharides, oligosaccharides, disaccharides, saccharides, gelatin, polyvinylpyrrolidone, polyethylene glycol, other binders, flavorants, colorants, magnesium stearate, other antiadherent agents, other stearate salts, sweeteners, silica, and other lubricants.

The composition can be administered according to any dosing regimen. Particular details of how administering is to be performed are within the ability of the person of ordinary skill in the art having the benefit of the present disclosure. In one embodiment, the administering is performed once or twice daily.

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Use of Sodium Nitrite as an Alternate Source of Nitric Oxide in Muscle Training

Exercising muscle demands increased blood flow in order to maintain sufficient nutrients and oxygen for metabolism. Nitric oxide is the body's most potent vasodilator. Nitric oxide is produced in the body by the enzyme nitric oxide synthase (NOS). NOS enzymes produce .NO by catalyzing a five electron oxidation of a guanidino nitrogen of L-arginine (L-Arg). Oxidation of L-Arg to L-citrulline occurs via two successive monooxygenation reactions producing $N^\omega$-hydroxy L-arginine as an intermediate. Two moles of $O_2$ and 1.5 moles of NADPH are consumed per mole of .NO formed (Liu, Q. and G. S. S., *Binding sites of nitric oxide synthases*. Methods Enzymol, 1996. 268: p. 311-324). NOS enzymes are the only enzymes known to simultaneously require five bound cofactors/prosthetic groups: FAD, FMN, heme, tetrahydrobiopterin ($BH_4$) and $Ca^{2+}$-calmodulin (CaM). All NOS isozymes are catalytically self-sufficient provided all required substrates and co-factors are available. CaM binding to nNOS has been shown to regulate catalytic activity by triggering electron flux from FMN to heme, thereby coupling the oxygenase and reductase domains. CaM also facilitates NADPH dependent reduction of cytochrome c and ferricyanide in $BH_4$ and heme depleted nNOS. If any of the co-factors become limiting, then NO production from NOS shuts down, and in many cases NOS then produces superoxide instead. This is indeed a very complex and coordinated effort to enzymatically produce NO which normally proceeds very efficiently. However, in disease characterized by oxidative stress where cofactors become oxidized, NOS uncoupling, or conditions of hypoxia where oxygen is limiting, this process can no longer maintain NO production. Therefore there has to be an alternate route to NO production. It is highly unlikely that Nature devised such a sophisticated mechanism of NO production as a sole source of a critical molecule. Nitrite reduction then acts as a backup system to the NOS system. Part of this may occur through nitrite reduction during low oxygen availability. Nitrite supplementation can then support NO production during exercise when enzymatic NO production is shut down.

Nitrite reduction to NO can occur via a simple mechanism. The 1-electron reduction of nitrite can occur by ferrous heme proteins (or any redox active metal) and an electron donor through the following reaction:

$$NO_2^- + Fe^{(II)} + H^+ \leftrightarrow NO + Fe^{(III)} + OH^-$$

This is the same biologically active NO as that produced by NOS just instead of using L-arg as the substrate, nitrite is used. Therefore for this to occur, the tissues or biological compartment must have a sufficient pool of nitrite stored. Nitrite supplementation may therefore act as a protective measure to compensate for insufficient NOS activity under conditions of hypoxia such as during anaerobic metabolism during exercise or muscle training. Nitrite contributes to whole body NO production and homeostasis. Considerable published support for this theory derives from the following facts: NO produced from nitrite in the upper intestine is up to 10,000 times the concentrations that occur in tissues from enzymatic synthesis (McKnight, G. M., et al., *Chemical synthesis of nitric oxide in the stomach from dietary nitrate in humans*. Gut, 1997. 40(2): p. 211-214), nitrite can act as a circulating NO donor (Dejam, A., et al., *Emerging role of nitrite in human biology*. Blood Cells Mol Dis, 2004. 32(3): p. 423-429) and nitrite can itself perform many actions previously attributable to NO (Gladwin, M. T., et al., *The emerging biology of the nitrite anion*. Nature Chemical Biology, 2005. 1(6): p. 308-314) without the intermediacy of NO (Bryan, N. S., et al., *Nitrite is a signaling molecule and regulator of gene expression in mammalian tissues*. Nature Chemical Biology, 2005. 1(5): p. 290-297). While L-arginine supplementation may provide moderate amounts of NO prior to workout, during a workout, this system becomes inefficient and very little NO from L-arginine can be produced due to lack of oxygen substrate. Therefore NO from nitrite provides an alternate mechanism to maintain NO production during exercise. Supplemental nitrite taken 15-20 minutes prior to workout can titrate up tissue and muscle nitrite concentrations in order to produce NO locally during exercise and therefore enhance blood flow and performance.

Nitrite Reduction to NO is an Oxygen Sensitive Process

Much of the recent focus on nitrite physiology is due to its ability to be reduced to NO during ischemic or hypoxic events (Lundberg, J. O. and E. Weitzberg, *NO generation from nitrite and its role in vascular control*. Arterioscler Thromb Vasc Biol, 2005. 25(5): p. 915-22; Bryan, N. S., *Nitrite in nitric oxide biology: Cause or consequence? A systems-based review*. Free Radic Biol Med, 2006. 41(5): p. 691-701; Bryan, N. S., et al., *Cellular Targets and Mechanisms of Nitros(yl) ation: An Insight into Their Nature and Kinetics in vivo*. Proc. Natl. Acad Sci. USA, 2004. 101(12): p. 4308-4313). Nitrite reduction to NO under aerobic and anaerobic conditions using chemiluminescent detection of free NO has been quantified and characterized. Under aerobic conditions, established by continuous sample purging with air, NO production by blood-free tissues and RBCs from nitrite was minimal and fleeting. However, switching the purge gas to $N_2$ (i.e., hypoxia) acutely enhanced tissue NO formation from $NO_2^-$ (FIG. 1, left). Hypoxic tissue $NO_2^-$ reduction exhibited compartment-specific properties (initial kinetics, amount, duration) and was most dramatic and sustained in liver homogenate. In addition to liver, all tissues sampled were capable of detecting an imposed decrease in $O_2$ tension and transducing this information into a potentiation of tissue NO formation from $NO_2^-$, as demonstrated by the marked, tissue-selective increases in NO production from $NO_2^-$ observed under aerobic (21% $O_2$) vs. hypoxic ($N_2$) conditions (FIG. 1, right). Heart, liver, skeletal (gastrocnemius) muscle, and aorta exhibited the greatest capacity for $NO_2^-$ reduction to NO during $O_2$ deprivation (FIG. 1, right inset). These data demonstrate an intrinsic ability of tissues to sense the graded diminution of ambient $O_2$ and transduce this information into the subsequent production of NO from $NO_2^-$. This finding suggests that various tissues might auto-regulate their blood flow in disease states with a pathological component of $O_2$ insufficiency through their capacity for hypoxic $NO_2^-$ reduction to NO provided sufficient nitrite exist.

Example 2

Nitrite can Protect Tissues From Ischemia-Reperfusion Injury

Figure 2:
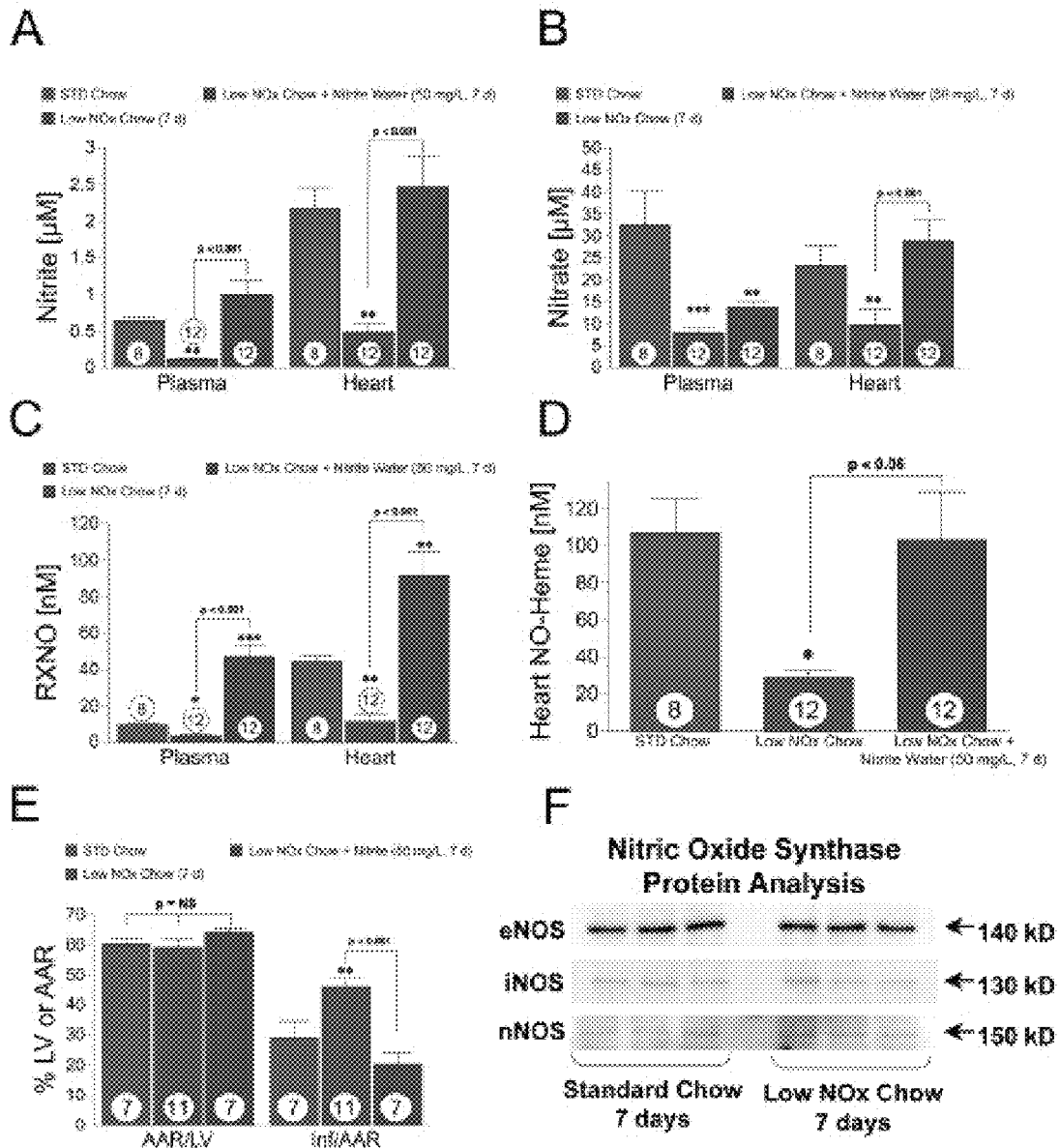
FIG. 2. Steady-state plasma and heart NOx and nitros(yl)ation levels in mice following nitrite insufficiency and supplementation. Mice were fed a standard rodent chow or a low NOx chow±50 mg/L nitrite supplementation for 7 days at which time steady-state levels of plasma and heart nitrite (A), nitrate (B), nitroso (C), and heart nitrosyl-heme (D) were measured. Mice fed a low NOx diet for 7 days exhibited an exacerbated injury following myocardial ischemia/reperfusion (I/R) (E) which was reversed in those animals supplemented with nitrite. Representative immunoblots of eNOS, iNOS, and nNOS from myocardial tissue homogenates of mice on standard chow and low NOx diet for 7 days reveal no changes in NOS protein expression, (F). These data demonstrate that supplemental nitrite can protect the heart from damage following heart attack.

There is a growing appreciation that nitrite therapy may provide benefit from I/R injury (Dezfulian, Raat et al. 2007). However, there are no data on the effects of nitrite insufficiency in the setting of I/R injury. Analysis of several different standard rodent chows revealed that Purina 5001 contains the highest concentrations of NOx (104.3±4.7 pmol/g nitrite and 6275±50.7 pmol/g nitrate) and nitroso as compared to any other standard rodent chow analyzed. Therefore this diet was used in comparison to mice fed a purified amino acid diet, the diet lowest in NOx (20.5±0.7 pmol/g nitrite and 503.1±17.9 pmol/g nitrate) but with the same L-arginine content. In order to reveal the biochemical and physiological effects of dietary nitrite insufficiency, mice were fed a standard rodent chow (Purina 5001) for 9 weeks and then switched to a purified amino acid diet low in nitrite and nitrate (Harlan TD99366) for 7 days. Control mice were fed Purina 5001 for 10 weeks. Consistent with an earlier report (Bryan, Fernandez et al. 2005), the low NOx diet significantly decreased plasma and heart steady-state nitrite and nitrate concentrations which could be restored by the addition of 50 mg/L nitrite in the drinking water for 1 week (FIG. 2A-B). Blood and tissue nitroso products have been shown to preserve NO bioactivity (Stamler, Simon et al. 1992) and protein nitrosation modification confer cGMP-independent NO signalling events (Stamler, Lamas et al. 2001). Changes in dietary nitrite consumption affect cellular signaling events (Bryan, Fernandez et al. 2005). Mice fed a low NOx diet for 1 week demonstrated a significant reduction in plasma and heart nitroso levels compared to mice fed standard chow, which could be replenished and increased with 50 mg/L nitrite in the drinking water for 1 week (FIG. 2C). Nitrosyl-heme products (FIG. 2D) were also reduced in the mice fed a low NOx diet and replenished by nitrite supplementation in the drinking water. These data reveal that changes in dietary nitrite and/or nitrate consumption can affect steady state concentrations of blood and tissue NO products/metabolites commonly used to assess NO production.

Whether dietary restriction of nitrite affected the severity of cardiac ischemia-reperfusion (I/R) injury was determined. The decrease in steady state nitrite concentrations in blood and heart was found to significantly exacerbate myocardial injury (FIG. 2E). The mice fed a low NOx diet displayed a 59% increase in infarct relative to the area at risk (AAR) compared to mice fed a standard chow. To ensure the observed effect was dependent upon NOx intake, and not due to an alteration in the nutritional value of the low NOx diet, a subset of mice on the low NOx diet were given 50 mg/L sodium nitrite ad libitum in the drinking water to restore steady state concentrations of blood and tissue nitrite. Nitrite supplementation in animals on the low NOx diet reversed the increased myocardial infarct size by 57%. Additionally, mice fed the low NOx diet displayed a higher mortality rate (57.7% survival) 24 hours post-myocardial infarction than mice on the standard rodent chow (70.6% survival) Likewise, survival improved in mice on the low NOx diet with nitrite-supplemented drinking water to 76.9%. Since nitrite is derived both from diet and oxidation of enzymatic NO production from NOS, potential compensatory changes in NOS expression following one week low NOx intake were investigated. Western blot analysis of myocardial tissue lysate revealed no significant alterations in NOS expression (eNOS, nNOS, and iNOS) (FIG. 2F). These data clearly suggest that the increased injury is due specifically to changes in steady state concentrations of plasma and heart nitrite as a result of decreased dietary NOx consumption and not from changes in enzymatic NO production.

Duranski et al. recently demonstrated that bolus addition of nitrite prior to reperfusion significantly protects the heart and liver from ischemia/reperfusion damage in an in vivo model (Duranski, M. R., et al., *Cytoprotective effects of nitrite during in vivo ischemia-reperfusion of the heart and liver*. J Clin Invest, 2005. 115(5): p. 1232-1240). During the ischemic event, NOS is inactive since oxygen, a necessary co-factor, has been depleted. It is believed that nitrite is reduced to NO to compensate for the insufficient NOS derived NO. These data are very important because they helped us to recognize that the application of exogenous nitrite has profound effects. Endurance training is known to cause ischemic organ damage in such organs as the gut and kidneys due to the diversion of blood flow from these organs to supply working muscles. This is a significant problem in marathon runners. Nitrite may provide a valuable nutrient to these athletes as a pre-workout or pre-marathon supplement to protect from ischemic injury during the event. Nitrite may then serve multiple purposes in the setting of myocardial ischemia/reperfusion. First, by titrating up tissue concentrations of nitrite when it is administered just prior to reperfusion, one can protect the heart from ischemia/reperfusion. Second, acute nitrite administration may initiate a signaling cascade that results in the upregulation of other protective proteins which afford protection hours later.

Figure 3:
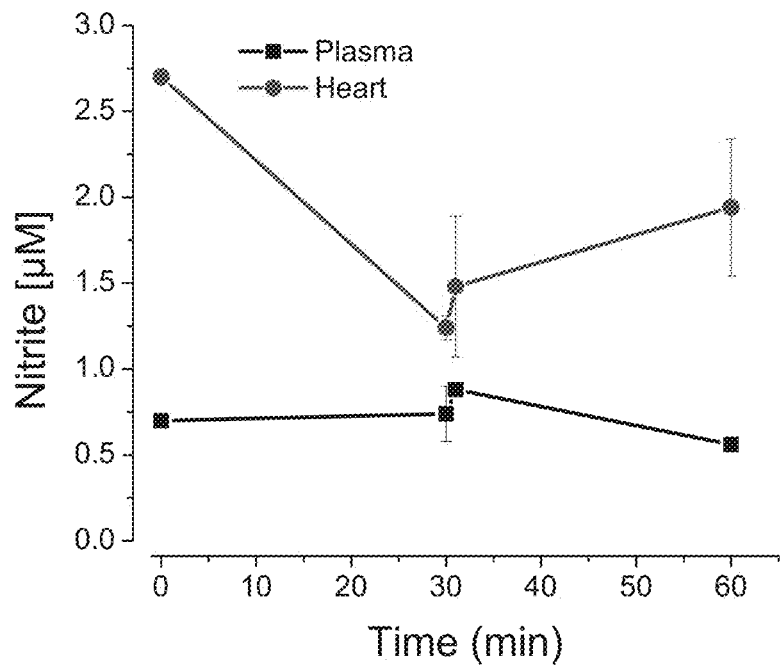
FIG. 3. Nitrite levels in heart tissue and plasma during 30 minutes of ischemia in a mouse model. These data demonstrate that nitrite is consumed during ischemia and restored during reperfusion.
Figure 3:
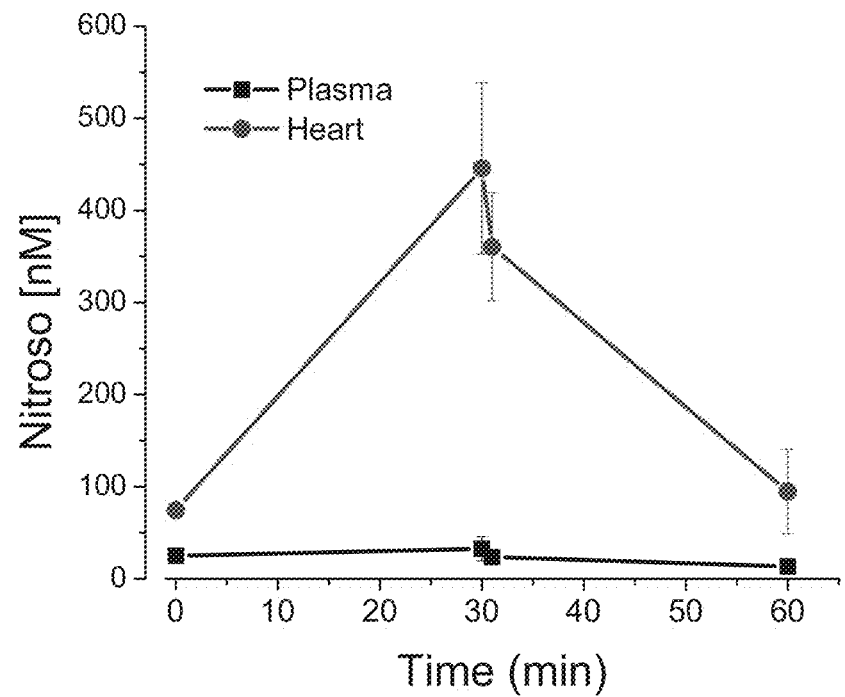

Nitrite has been shown to be protective in both the heart and the liver following ischemia/reperfusion (Webb, A., et al., *Reduction of nitrite to nitric oxide during ischemia protects against myocardial ischemia-reperfusion damage*. Proc Natl Acad Sci USA, 2004. 101(13683-13688); Duranski, M. R., et al., *Cytoprotective effects of nitrite during in vivo ischemia-reperfusion of the heart and liver*. J Clin Invest, 2005. 115(5): p. 1232-1240). It is speculated that nitrite is reduced to NO under ischemic conditions to provide an alternate source of NO when NOS is inactive due to decreased substrate delivery and decreased oxygen saturation. To better understand the fate of nitrite during ischemia and reperfusion, a time course of nitrite metabolism both after ischemia and during reperfusion was conducted. As shown in FIG. 3, nitrite is consumed in the heart tissue during 30 minutes of ischemia but is unaffected in the plasma. The consumption of nitrite appears to lead to a concomitant increase in cardiac nitroso products (FIG. 3B). Nitrite can form nitrosothiols in a first order reaction requiring heme and thiols and can also be reduced to NO under anaerobic conditions (Bryan, N. S., et al., *Nitrite is a signaling molecule and regulator of gene expression in mammalian tissues*. Nat Chem Biol, 2005. 1(5): p. 290-7). During reperfusion, nitrite is gradually increased and restored whereby tissue nitroso decompose during the reperfusion phase (FIG. 3). Without being bound by a particular theory, the inventor proposes that nitrite serves two functions in the setting of ischemia reperfusion. It may first serve as a NOS-independent source of NO by which nitrite is reduced to NO under ischemic conditions when NOS is inactive. Secondly, nitrite may react with critical thiols to form nitrosothiols. It is possible that this nitroso modification acts as a reversible protective shield which reduces irreversible oxidation during the oxidative burst of reperfusion. Aside from "capping" critical thiols from oxidation, and without being bound by a particular theory, the inventor proposes that the nitroso products can then release the $NO^+$ moiety during the reperfusion phase and act an a redox sensitive NO donor (Hogg, N., *Biological chemistry and clinical potential of S-nitrosothiols.* Free Radic Biol Med, 2000. 28(10): p. 1478-86). Biochemical data support this notion by the increase in nitroso at the expense of nitrite followed by the decay of nitroso over time during reperfusion. Therefore adding supplemental nitrite can increase plasma and tissue nitrite but also lead to an increase in steady state levels of nitroso and thereby afford protection during ischemia/reperfusion. On the contrary, nitrite insufficiency leads to increased injury because there is not enough stored in blood or tissue to perform these actions.

Figure 4:
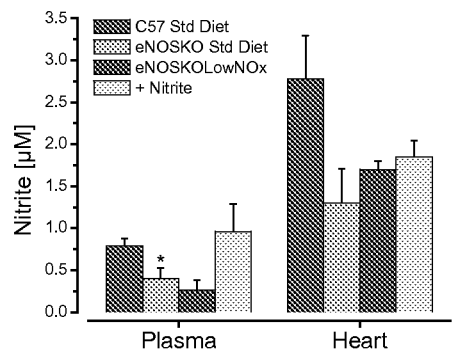
FIG. 4. Dietary nitrite insufficiency unmasks NO biochemistry (A) nitrite, (B) nitrate, (C) nitroso, and (D) NO-heme in eNOS knockout mice and is restored by supplementation in the drinking water. Methods: eNOS knockout mice on either standard diet or low NOx diet±50 mg/L nitrite supplementation were compared to C57 control mice on standard diet to reveal dietary nitrite can restore NO biochemistry in mice unable to produce NO.
Figure 4:
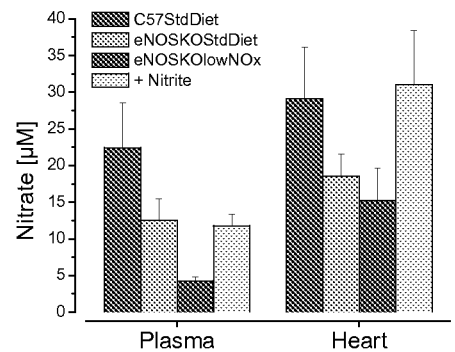
Figure 4:
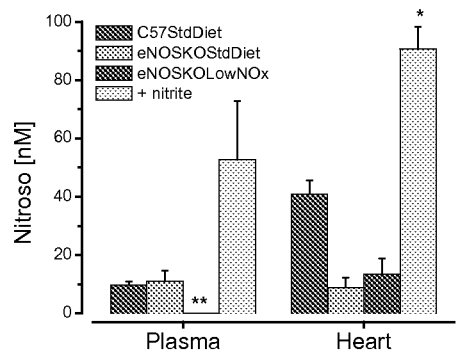
Figure 4:
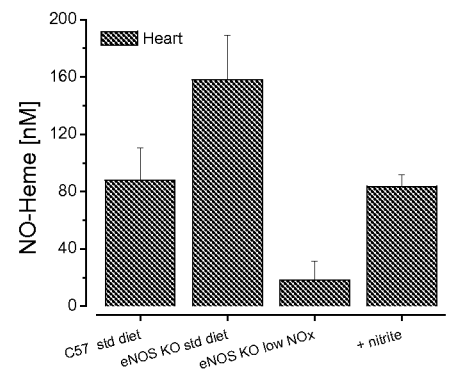

Enzymatic NO insufficiency is a hallmark of a number of diseases including cardiovascular disease. To test the hypothesis that dietary nitrite can compensate for NOS dysfunction, the above experiments were repeated in eNOS –/– mice. The mice were fed standard rodent chow or low NOx diet. As shown in FIG. 4, eNOS –/– mice revealed lower plasma nitrite concentrations consistent with earlier findings (Kleinbongard, P., et al., *Plasma nitrite reflects constitutive nitric oxide synthase activity in mammals.* Free Radical Biology & Medicine, 2003. 35(7): p. 790-796) but there is no significant difference in cardiac nitrite revealing that blood markers do not accurately reflect tissue status (Bryan, N. S., *Nitrite in nitric oxide biology: Cause or consequence? A systems-based review.* Free Radic Biol Med, 2006. 41(5): p. 691-701). Plasma nitrite could be further decreased by feeding eNOS–/– mice a low NOx diet demonstrating that plasma nitrite is a reflection of both NOS and diet. Feeding low NOx diet to eNOS–/– mice completely eliminated steady state concentrations of plasma nitroso without any significant effect on cardiac nitroso. Supplementation of 50 mg/L nitrite in the drinking water for 7 days restores plasma nitrite in eNOS–/– to control levels and increases both plasma and cardiac nitroso to above C57 control levels.

Mice deficient in eNOS have increased injury to ischemia/reperfusion insult (Jones, S. P., et al., *Myocardial ischemia-reperfusion injury is exacerbated in absence of endothelial cell nitric oxide synthase.* Am J Physiol, 1999. 276(5 Pt 2): p. H1567-73) and data shown above reveal these mice also have reduced nitrite and nitroso compared to C57 wild type. To investigate if dietary nitrite can benefit eNOS–/– mice, eNOS–/– mice on low NOx diet±50 mg/L nitrite in drinking water were subjected to 30 minutes ischemia and 24 hour reperfusion as above. These mice are also protected from myocardial ischemia/reperfusion injury suggesting that dietary nitrite supplementation can provide benefit under conditions of dysfunctional NOS.

Example 3

Nitrite can be Used to Delay or Prevent the Onset and Development of Atherosclerosis Initial studies in the characterization of the LDb mouse reveal that they have diminished blood and tissue nitrite and nitroso levels with no difference in nitrate at 11 months when atherosclerosis is well developed. These data indicate that there is deficiency in bioavailable NO and nitrite. Steady state tissue nitroso levels are also decreased suggesting a dysregulation of protein nitrosation and therefore provide the rationale and justification for early intervention of dietary nitrite supplementation on restoring NO-nitroso redox and on the progression of atherosclerosis.

Figure 5:
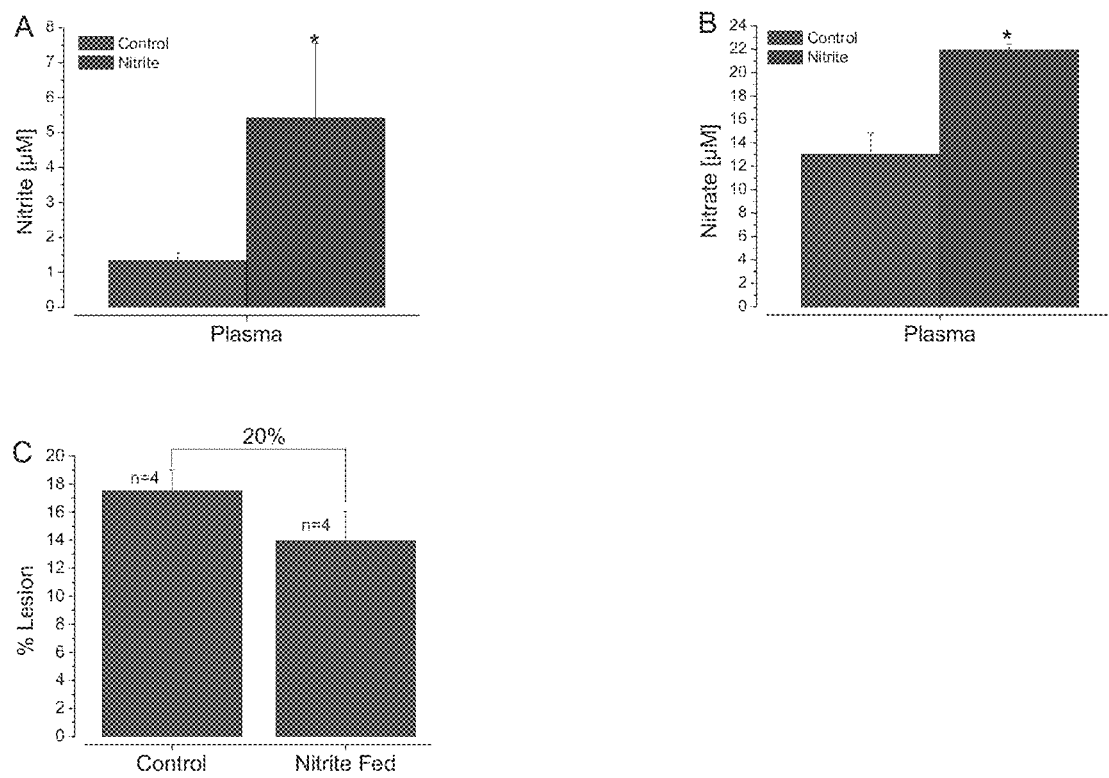
FIG. 5. Mice were fed 50 mg/L nitrite supplement for 12 weeks, resulting in increased circulating nitrite and nitrate levels (FIGS. 5A, 5B). The nitrite fed group had 20% less lesion formation on the abdominal aorta than the control group fed high fat diet with nitrite free water (FIG. 5C), demonstrating that nitrite supplementation can inhibit the progression of atherosclerosis in a mouse model of atherosclerosis.

In order to demonstrate the utility of supplemental nitrite in affecting the progression of atherosclerosis, a high fat diet was fed to 8 female LDb mice for 12 weeks. Four of the mice received nitrite free water and the other 4 mice were supplemented with 50 mg/L nitrite throughout the 12 weeks on high fat diet. Although the LDb mice spontaneously develop atherosclerosis on normal rodent chow, the addition of a high fat diet will accelerate the process from 8 months to 12 weeks. At the time of sacrifice, plasma was collected for nitrite, nitrate determination as well as lipid profile determination. As shown in FIG. 5A-B, there significantly more circulating nitrite and nitrate in the nitrite fed mice than the nitrite free water group. The nitrite fed group had 20% less lesion formation on the abdominal aorta than the control group fed high fat diet with nitrite free water (FIG. 5C). These data demonstrate that nitrite supplementation can inhibit the progression of atherosclerosis in the female LDb mice using a high fat diet.

Example 4

Specific Formulation for Extending Biological Half Life of Nitrite

Aim: To develop specific formulation that will extend the circulating half life of nitrite from 110 seconds to 45-60 minutes.

Methods: Since nitrite is derived from NO oxidation, diet, and from the reduction of nitrate in the human body, to enhance nitrite bioavailability, substrates from all 3 pathways were included: L-arginine to enhance NO production from nitric oxide synthase which will subsequently produce nitrite; sodium nitrite to increase acute circulating nitrite concentrations; ascorbic acid to inhibit endogenous nitrosation reactions in the stomach; and sodium nitrate to provide a slow release source of nitrite. This specific formulation was compared to 3 g L-arginine that is marketed commercially to enhance NO production. An intravenous line was obtained by the inventor on himself with 21 gauge infusion set needle and blood collected. The first 5 ml of blood was discarded. Blood was then collected at baseline. Then the prescribed formulation was dissolved in 50 ml of water and taken orally. A timer was started and blood was sampled for analysis at 1 minute and every 2 minutes for 60 minutes.

Figure 6:
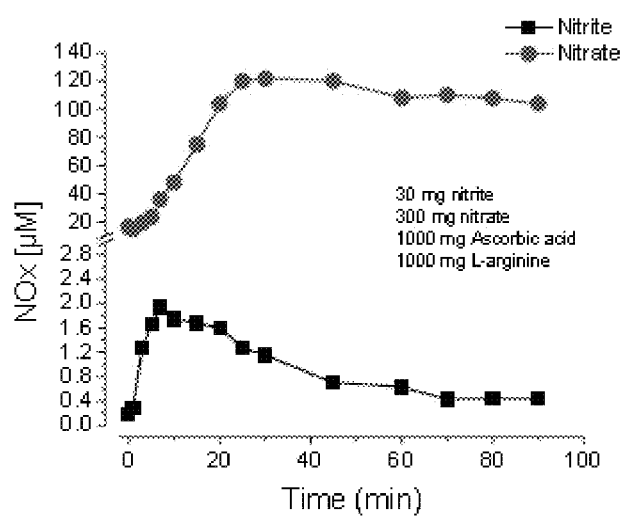
FIG. 6. Blood nitrite concentration after ingestion of an oral formulation containing sodium nitrite in a human model.
Figure 7:
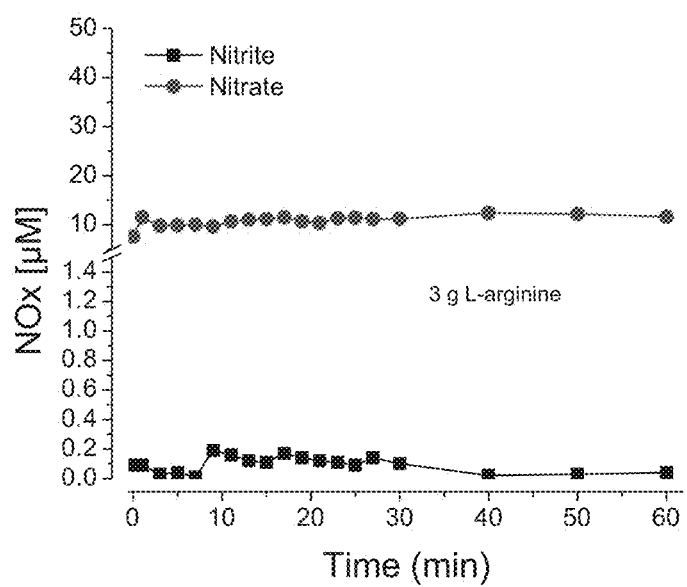
FIG. 7. Blood nitrate concentration after ingestion of an oral formulation containing L-arginine in a human model.

Results: Direct analysis of the volunteer's blood revealed that the oral formulation increases blood nitrite within 3 minutes and reaches a maximum 9 minutes (FIG. 6). This represents a 20 fold increase in plasma nitrite that lasts for 50 minutes. Plasma nitrate continues to rise throughout the course of the experiment. L-arginine in combination with NAD and ascorbic acid did not significantly affect plasma nitrite or nitrate concentrations (FIG. 7).

Conclusions: The specific formulation developed can increase plasma nitrite to therapeutic levels within 3 minutes of ingestion and can maintain therapeutic levels until 50 minutes after drinking. This represents a novel formulation whereby this product can be given immediately upon patient presentation of ischemic episode that will maintain the protective nitrite levels for up to 1 hour. There is a golden hour in clinical medicine whereby the patient survival and outcome from ischemic episodes greatly declines. The safety of nitrite and nitrate at these doses is well established and therefore the formulations according to several embodiments discussed above represent a safe, novel use for oral nitrite as a cardioprotective agent.

Example 5

Specific Formulations

Disclosed herein is an immediate and extended release form of nitrite extending the biological half life from hundreds of seconds to minutes and hours. Among others, two possible applications for this technology may be as a revolutionary nitric oxide based supplement for the workout industry and a daily supplement to restore NO homeostasis in the aging population. Below is a range of effective doses of each ingredient.

Workout Supplement and Daily Supplement
Sodium nitrite (0.01 mg/kg-15 mg/kg: fatal dose is 22-23 mg/kg in humans)
Sodium nitrate (1.0 mg/kg-50 mg/kg; Poisoning in man may result from a total oral daily dose in excess of 4 g or from a single dose of more than 1 g. 8 g may be fatal and 13-15 g are generally fatal (Sollmann, 1957). Although natural sources of nitrate are available, the concentrations are sufficiently low that the volume (or mass) that would need to be consumed to provide the same degree of supplementation as compared to several embodiments disclosed herein would be prohibitively large. For example, one liter of beetroot juice contains about 2.79 g of nitrate.
Ascorbic acid (1 mg/kg-25 mg/kg)
L-arginine (2 mg/kg-50 mg/kg)
In one embodiment, a workout supplement formulation to enhance NO formation in working muscle consists, consists essentially of or comprises:
40 mg sodium nitrite
250 mg sodium nitrate
1000 mg ascorbic acid
1000 mg L-arginine
In another embodiment, a workout supplement formulation to enhance NO formation in working muscle consists, consists essentially of or comprises:
30 mg sodium nitrite
300 mg sodium nitrate
1000 mg ascorbic acid
1000 mg L-arginine
In one embodiment, a daily supplement formulation to restore NO homeostasis consists, consists essentially of or comprises:
20 mg sodium nitrite
150 mg sodium nitrate
500 mg ascorbic acid
500 mg L-arginine
FIG. 6 shows blood nitrite and nitrate levels from 0 min to 60 min after ingestion of an oral formulation containing 30 mg sodium nitrite, 300 mg sodium nitrate, 1000 mg ascorbic acid, and 1000 mg L-arginine in a human volunteer. In one embodiment, the formulation consists, consists essentially of or comprises 30 mg sodium nitrite, 300 mg sodium nitrate, 1000 mg ascorbic acid, and 1000 mg L-arginine.

Example 6

NO Generation Without NO Synthase

In 1994 two groups independently presented evidence for generation of NO in the stomach resulting from the acidic reduction of inorganic nitrite (Benjamin, N., F. O'Driscoll, et al. (1994). "Stomach NO synthesis." *Nature* 368(6471): 502; Lundberg, J. O., E. Weitzberg, et al. (1994). "Intragastric nitric oxide production in humans: measurements in expelled air." *Gut* 35(11): 1543-6). Benjamin and colleagues demonstrated that the antibacterial effects of acid alone was markedly enhanced by addition of nitrite which is present in saliva whereas Lundberg and colleagues could measure high levels of NO in expelled air from the stomach in humans. These levels were abolished after pretreatment with a proton pump inhibitor and markedly increased after ingestion of nitrate, showing the importance of both luminal pH and the conversion of nitrate to nitrite for stomach NO generation. These were the first reports of NO synthase-independent formation of NO in vivo.

In the classical NO synthase pathway, NO is formed by oxidation of the guanidino nitrogen of L-arginine with molecular oxygen as the electron acceptor (Moncada, S. and A. Higgs (1993). "The L-arginine-nitric oxide pathway." *N Engl J Med* 329(27): 2002-12). This complex reaction is catalysed by specific heme-containing enzymes, the NO synthases, and the reaction requires several co-factors. The alternative pathway was fundamentally different; instead of L-arginine it used the simple inorganic anions nitrate ($NO_3^-$) and nitrite ($NO_2^-$) as substrates in a stepwise reduction process that did not require NO synthase or multiple co-factors. The biochemical pathway and biological effects of nitrate reduction to nitrite and further on to NO in the gastrointestinal tract have now been further characterized (Lundberg, J. O., E. Weitzberg, et al. (2004). "Nitrate, bacteria and human health." *Nat Rev Microbiol* 2(7): 593-602). Oral commensal bacteria are essential for the first step in the nitrate-nitrite-NO pathway since they are responsible for the reduction of the higher nitrogen oxide nitrate to form nitrite. It was known from the literature that the salivary glands extract nitrate from plasma but the reason for this active process was not explained. This active process leads to levels of salivary nitrate that are 10-20 fold higher than in plasma. Oral facultative anaerobic bacteria residing mainly in the crypts of the tongue, then reduce nitrate to nitrite by the action of nitrate reductase enzymes (Spiegelhalder, B., G. Eisenbrand, et al. (1976). "Influence of dietary nitrate on nitrite content of human saliva: possible relevance to in vivo formation of N-nitroso compounds." *Food Cosmet Toxicol* 14: 545-548; Duncan, C., H. Dougall, et al. (1995). "Chemical generation of nitric oxide in the mouth from the enterosalivary circulation of dietary nitrate [see comments]." *Nat Med* 1(6): 546-51). These bacteria use nitrate as an alternative electron acceptor to gain ATP in the absence of oxygen. This highly effective bacterial nitrate reduction results in salivary levels of nitrite that are 1000-fold higher than those found in plasma (Lundberg, J. O. and M. Govoni (2004). "Inorganic nitrate is a possible source for systemic generation of nitric oxide." *Free Radic Biol Med* 37(3): 395-400). When nitrite-rich saliva meets the acidic gastric juice, nitrite is protonated to form nitrous acid ($HNO_2$) which then decomposes to NO and a variety of other nitrogen oxides (Benjamin, O'Driscoll et al. 1994; Lundberg, Weitzberg et al. 1994). It is now established that oral commensal bacteria are pivotal in gastric NO formation, and gastric NO levels are consistently low in animals reared under complete germ-free conditions (Sobko, T., C. Reinders, et al. (2004). "Gastrointestinal nitric oxide generation in germ-free and conventional rats." *Am J Physiol Gastrointest Liver Physiol* 287(5): G993-7). If the oral flora is selectively removed by topical treatment with an antibacterial mouthwash, the gastric NO levels decrease drastically (Petersson, J. (2008). Nitrate, nitrite and nitric oxide in gastric mucosal defense. *Uppsala University*. Uppsala, Sweden). This pathway is now known to contribute to at least half of the endogenous NO metabolism in humans.

A Novel Nitric Oxide System: This recognition now provides a new paradigm for restoring NO homeostasis that is vastly different than the NOS system. The stepwise reduction of nitrate to nitrite to nitric oxide is, by necessity, an inefficient process by which each step yields a 3-log lower concentration of product than substrate (Jansson, E. A., L. Huang, et al. (2008). "A mammalian functional nitrate reductase that regulates nitrite and nitric oxide homeostasis." *Nat Chem Biol* 4(7): 411-7). Steady state levels of nitrate and nitrite in healthy humans is 20-40 μM and ~0.5 μM respectively. The relative ratio of nitrate to nitrite in blood corroborates this 3-log reduction efficacy of nitrate to nitrite. Given this same efficiency for nitrite, one might expect ~5 nM NO production from reduction of physiological concentrations of nitrite, which would certainly elicit a physiological response. However, we have found that oxygen is a potent inhibitor of nitrite reduction with 80% inhibition at 0.5% oxygen (Feelisch, M., B. O. Fernandez, et al. (2008). "Tissue Processing of Nitrite in Hypoxia: An Intricate Interplay of Nitric Oxide-Generating and -Scavenging Systems." *J Biol Chem* 283(49): 33927-34). In vitro measurements indicate only 0.01% of nitrite is converted to NO in completely anaerobic and anoxic tissue homogenates and actually much less at physiological concentrations of oxygen (Bryan, N. S., B. O. Fernandez, et al. (2005). "Nitrite is a signaling molecule and regulator of gene expression in mammalian tissues." *Nat Chem Biol* 1(5): 290-7). Since humans with known cardiovascular risk factors and endothelial dysfunction have reduced plasma and presumably tissue levels of nitrite (Kleinbongard, P., A. Dejam, et al. (2006). "Plasma nitrite concentrations reflect the degree of endothelial dysfunction in humans." *Free Radic Biol Med* 40(2): 295-302), this reservoir of NO activity is further compromised and therefore unable to be utilized for NO production by inherent biological systems. As a result, in order to get an appreciable amount of NO from this pathway, pharmacological doses of nitrate and nitrite are needed when relying simply on inherent biological systems for the reduction.

Although both nitrite and nitrate are naturally occurring molecules and are part of our food supply (Hord, N. G., Y. Tang, et al. (2009). "Food sources of nitrates and nitrites: the physiologic context for potential health benefits." *Am J Clin Nutr* 90(1): 1-10), they are not without toxicity. We have created a system whereby we can enhance the nitrate-nitrite-NO reduction efficacy at each step which justifies the use of physiological concentrations of nitrate and nitrite as a provision of NO which can overcome the body's inability to generate NO from L-arginine.

Remarkably, we have identified natural products that are part of our normal diet which can enhance this pathway. We recently completed a nationwide survey of over 400 food products including meats and vegetables, both organically and conventionally grown and screened over 100 herbs that have been used for many years in traditional medical practices in Europe and Asia. The results of our study have revealed products that are enriched in nitrate (e.g., beet root) that provide the substrate nitrite in the pathway. We have also uncovered a select few herbs with very robust nitrite reductase activity that is unaffected by oxygen (e.g., Hawthorne berry).

Figure 8:
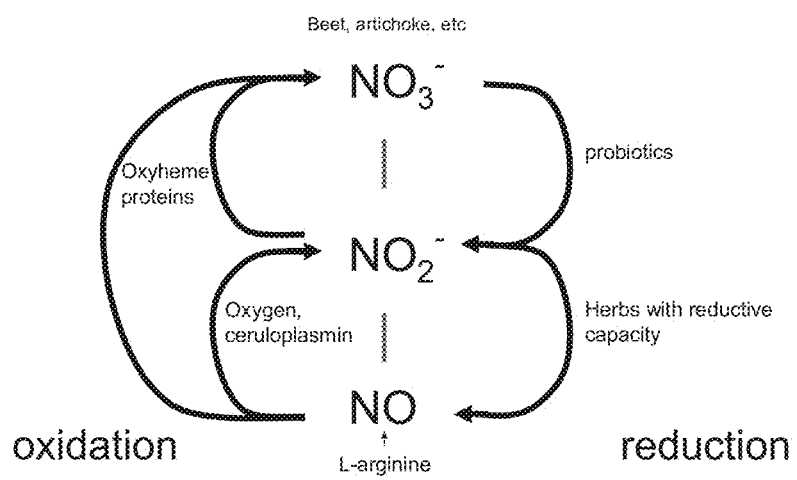
FIG. 8. Oxidation and reduction of nitrate, nitrite, and nitric oxide.

As illustrated in FIG. 8. the endogenous production of nitric oxide by NOS leads to the rapid oxidation to nitrite by molecular oxygen and plasma proteins such as ceruloplasmin. Alternatively, NO reacts directly with oxyheme-proteins such as hemoglobin and is oxidized to nitrate. We now have a system to reverse this process and regenerate NO from these oxidative end-products, nitrite and nitrate. The introduction of beet and Hawthorne provide a very robust system for generating NO that is novel and innovative and allows us to use much lower physiological concentrations of nitrite rather than pharmacological therapeutic doses.

We recently published our initial results from these investigations using Traditional Chinese Medicines (TCM) (Tang, Y., H. Garg, et al. (2009). "Nitric oxide bioactivity of traditional Chinese medicines used for cardiovascular indications." *Free Radic Biol Med* 47(6): 835-40). Since many of these TCMs are used primarily for cardiovascular indications characterized by NO insufficiency, we hypothesized that some, if not all, of these TCMs have a robust NO bioactivity that may act to restore NO homeostasis. The results from our study reveal that the herbs tested contained varying levels of nitrite and nitrate and varying nitrite reductase activity. Several of the herbal extracts contain a nitrite reductase activity greater by 1000 times than that of biological tissues (Feelisch, Fernandez et al. 2008). We have discovered that Hawthorn berry contains an active nitrite reductase that is 10 times more active than the Chinese herbs we tested.

We concluded that repletion of biological nitrite and nitrate by these extracts and providing a natural system for NO generation in both endothelium-dependent and -independent mechanisms may account for some of the therapeutic effects of TCMs (Tang, Garg et al. 2009). Since all of these herbs and TCMs contain relatively high levels of nitrate and some residual nitrite, there is in essence over 5000 years of phase I safety trials in humans regarding nitrite and nitrate at these levels.

Figure 9:
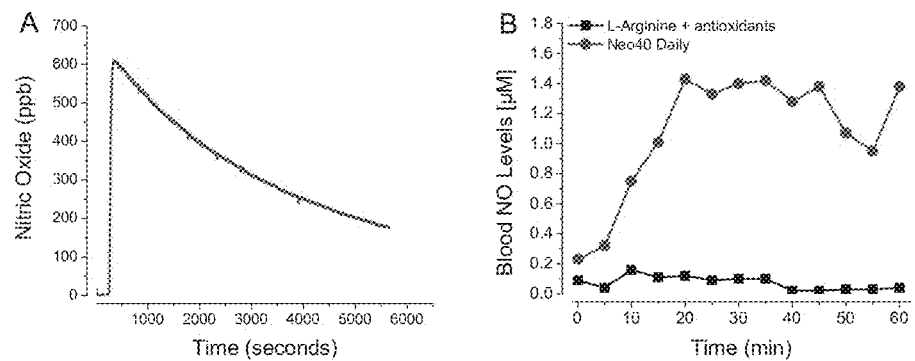
FIG. 9. Effect of a composition according to the present invention on NO concentration and blood NO levels compared to blood NO levels from a nutritional supplement containing L-arginine and antioxidants.

Human data: Based on the pre-clinical data obtained from above we created a rationally designed formulation based on the ingredients with the greatest capacity for generating NO through the system in FIG. 8. Over two years of screening and testing a number of combinations of different herbs, we recognized a combination of beet root and hawthorne berry which gave us the most predictable and prolonged NO release profile. The NO release kinetics are shown in FIG. 9A. In this in vitro system, the NO product has a half life of roughly 1 hour with respect to NO release.

The following formulation (Neo40) was prepared:
beet root powder, 200 mg;
hawthorn berry extract, 100 mg;
sodium nitrite, 20 mg;
L-citrulline, 100 mg;
vitamin B12, 1000 μg (as methylcobalamin and cyanocobalamin);
vitamin C, 100 mg (as magnesium ascorbate and ascorbic acid); and
about 250 mg to about 500 mg other ingredients (mannitol, modified cellulose, xylitol, natural orange flavor, magnesium stearate, sucralose, and silica).

Neo40 was sourced and developed into a quick dissolving lozenge by a GMP-certified facility. We then tested the pharmacokinetics of Neo40 in humans. When allowed to dissolve in the mouth, Neo40 leads to a slow and steady rise in plasma nitrite of humans as shown in FIG. 9B. To demonstrate the difference between Neo40 and compositions of L-arginine and anti-oxidants that have been used as nutritional supplements designed to enhance NO production, we compared Neo40 to one of the most popular products on the market. As shown in FIG. 9B, the L-arginine product did not lead to any appreciable formation of NO when consumed. This is in stark contrast to the NO formation resulting from administration of Neo40.

Figure 10:
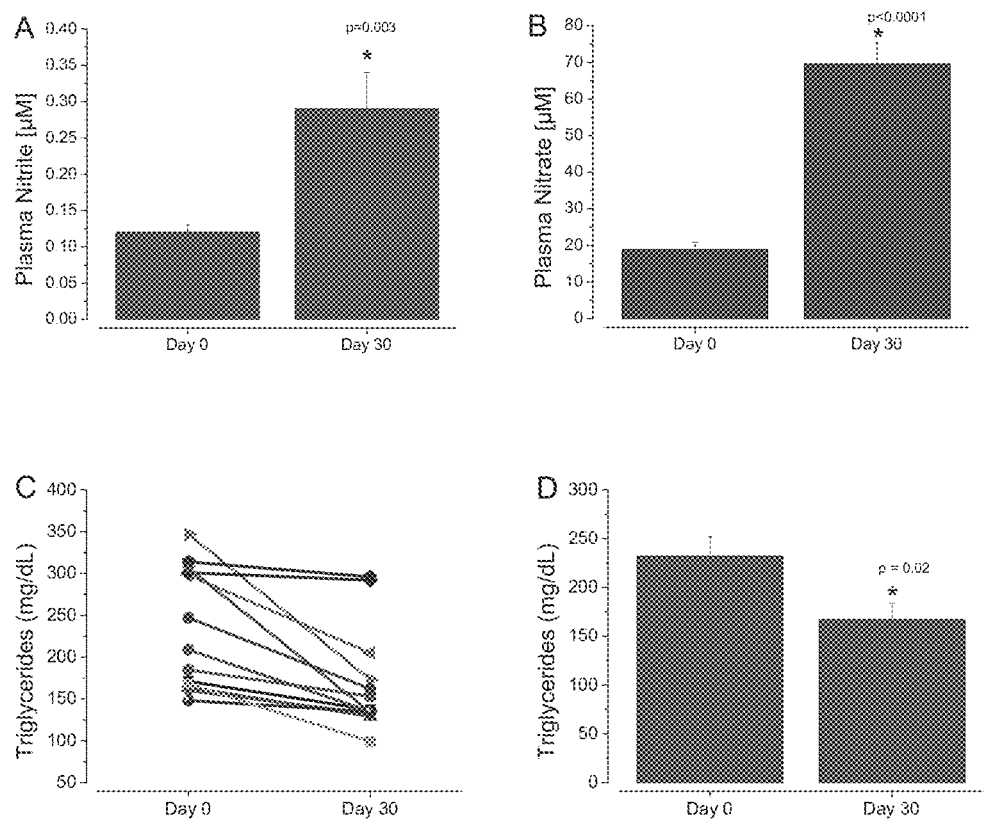
FIG. 10. (A&B) A 30 day twice per day regimen of a composition according to the present invention significantly increase plasma levels of nitrite and nitrate to normal healthy levels; (C) Patients taking a composition according to the present invention daily for 30 days saw a 10%-55% decrease in fasting triglycerides. (D) Collectively all patients taking a composition according to the present invention daily experienced a statistically significant reduction in fasting triglycerides (data are ave±SEM of n=13 patients)

In order to demonstrate that Neo40 could restore NO levels, we conducted a small clinical trial in healthy volunteers (age 34-64; 6 male, 6 female; 6 smokers, 6 non-smokers) and found that after taking Neo40 (one lozenge, twice a day) for 30 days lead to a modest but significant increase in both plasma nitrite and nitrate (FIG. 10A-B).

Based on this data, we began a clinical trial. Our inclusion criteria for this double-blinded, placebo-controlled study were patients over 40 with three or more of the following cardiovascular risk factors: hypertension, obesity, hyperlipidemia, smoking, sedentary lifestyle, family history of cardiovascular disease, and diabetes. As shown in FIG. 10C, there was a modest to dramatic decease in triglycerides in the patients with elevated triglycerides>149 mg/dL). As shown in FIG. 10D, 100% of the patients with elevated triglycerides (>149 mg/dL) at baseline had a reduction in their triglycerides with the twice-daily regimen. Utilizing beet root and Hawthorne berry along with nitrite and L-citrulline provides a novel system for generating NO whereby the metabolism of nitrite is specifically directed towards reduction to NO by the Hawthorne berry. Though not to be bound by theory, we believe the presence of an active reductase in the formulation is an important addition as it allows a more efficient means to produce NO from nitrite.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of reducing a patient's triglyceride level, comprising:
    administering to the patient a composition in a form of a lozenge dissolvable in the mouth, the composition comprising:
        from about 40 weight parts to about 1000 weight parts of a botanical nitrate source;
        from about 20 weight parts to about 500 weight parts of a botanical source of nitrite reduction activity;
        from about 20 weight parts to about 500 weight parts L-citrulline; and
        from about 4 weight parts to about 100 weight parts of a nitrite salt.

2. The method of claim 1, wherein the botanical nitrate source is selected from the group consisting of beet root, artichoke, holy basil, gingko, and mixtures thereof and is present at about 200 weight parts;
    the botanical source of nitrite reduction activity is selected from the group consisting of hawthorn berry, Schisandra, green tea, beet root, pine bark, and mixtures thereof and is present at about 100 weight parts;
    the L-citrulline is present at about 100 weight parts; and
    the nitrite salt is selected from the group consisting of sodium nitrite, potassium nitrite, and mixtures thereof and is present at about 20 weight parts;
    and the composition further comprises:
    about 1 weight part vitamin B12 in a form selected from the group consisting of methylcobalamin, cyanocobalamin, and mixtures thereof;
    about 100 weight parts vitamin C in a form selected from the group consisting of magnesium ascorbate, ascorbic acid, and mixtures thereof; and
    from about 50 weight parts to about 1500 weight parts of one or more ingredients selected from the group consisting of mannitol, xylitol, sorbitol, sugar alcohols, cellulose, cellulose esters, cellulose ethers, starch, polysaccharides, oligosaccharides, disaccharides, saccharides, gelatin, polyvinylpyrrolidone, polyethylene glycol, binders, flavorants, colorants, magnesium stearate, anti-adherent agents, stearate salts, sweeteners, silica, and lubricants.

3. The method of claim 2, wherein the lozenge weighs from about 600 mg to about 2000 mg.

4. The method of claim 2, wherein the administering is performed once or twice daily.

* * * * *